(12) United States Patent
Hoffman et al.

(10) Patent No.: US 10,741,274 B2
(45) Date of Patent: Aug. 11, 2020

(54) METHODS AND SYSTEMS FOR COLLECTING PHARMACEUTICAL CONTAINERS

(71) Applicant: EXPRESS SCRIPTS, INC., St. Louis, MO (US)

(72) Inventors: Robert Hoffman, Linden, IN (US); Jonathan Joplin, Chesterfield, MO (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 745 days.

(21) Appl. No.: 15/434,825

(22) Filed: Feb. 16, 2017

(65) Prior Publication Data
US 2018/0232497 A1 Aug. 16, 2018

(51) Int. Cl.
*B65G 1/137* (2006.01)
*G16H 20/10* (2018.01)
*G16H 40/20* (2018.01)

(52) U.S. Cl.
CPC ............. *G16H 20/10* (2018.01); *G16H 40/20* (2018.01)

(58) Field of Classification Search
CPC .................................. G16H 20/10; B65G 1/137
See application file for complete search history.

(56) References Cited

U.S. PATENT DOCUMENTS

| | | | |
|---|---|---|---|
| 5,660,305 A | 8/1997 | Lasher et al. | |
| 5,720,154 A | 2/1998 | Lasher et al. | |
| 5,771,657 A | 6/1998 | Lasher et al. | |
| 6,769,228 B1 | 8/2004 | Mahar | |
| 6,892,512 B2 | 5/2005 | Rice et al. | |
| 7,185,477 B2 | 3/2007 | Rice et al. | |
| 7,995,831 B2 | 8/2011 | Eller et al. | |
| 8,799,016 B1 * | 8/2014 | Cohan | G06Q 10/109 705/2 |
| 9,242,751 B1 | 1/2016 | Joplin et al. | |
| 9,567,119 B2 | 2/2017 | Joplin | |
| 9,710,866 B2 * | 7/2017 | Luciano, Jr. | B65D 75/5888 |
| 2009/0288996 A1 * | 11/2009 | Shafer | B65G 1/1378 209/546 |

* cited by examiner

*Primary Examiner* — Jonathan Snelting

(57) ABSTRACT

A pharmaceutical order filling system receives pharmaceutical orders and uses an accumulation device to accumulate bottles of pharmaceuticals corresponding to the pharmaceutical orders. The accumulation device is configured with a table assembly that includes a plurality of holding tubes configured to accumulate multiple bottles corresponding to pharmaceutical orders. The accumulation device also includes a bottle pick and place assembly configured to place bottles into holding tubes and an unload assembly configured to empty accumulated bottles from holding tubes into an unload assembly tube. The accumulation device may be further configured to receive and temporarily store a single bottle of a prescription order. The accumulation device may be configured to release accumulated bottles onto a conveyor in an upright position.

27 Claims, 17 Drawing Sheets

METHODS AND SYSTEMS FOR COLLECTING PHARMACEUTICAL CONTAINERS

FIELD

The present disclosure relates generally to the technical field of automated filling centers. In a specific example, the present disclosure may relate to a high volume fulfillment center, (e.g., a high volume pharmacy) and to systems and devices used in filling prescriptions and prescription orders at a high volume pharmacy.

BACKGROUND

A high-volume pharmacy may process and fill a large number of prescriptions and prescription orders. Automated systems may be used by a high volume pharmacy to process and fulfill prescriptions.

Frequently, more than one prescription drug is required to complete a prescription order. Portions of the prescription order may be fulfilled in different areas of the high-volume pharmacy. After fulfillment, the fulfilled prescriptions may be gathered into a complete prescription order for shipping.

DETAILED DESCRIPTION

Example systems and methods for collecting pharmaceutical containers, such as for shipment or other delivery, are described. In the following description, for purposes of explanation, numerous specific details are set forth in order to provide a thorough understanding of example embodiments. It will be evident, however, to one of ordinary skill in the art that embodiments may be practiced without these specific details.

Generally, a prescription order is generated for a high volume pharmacy. The prescription order may include one or more than one prescription drug for fulfillment. Each prescription drug in a prescription order is an order component of the prescription order. Generally, the order components are pill containers or containers and packaging having a quantity of a prescription drug contained therein.

Multiple order components of a prescription order may be prepared at different times. The steps required for preparation, quality control, or otherwise reviewing or processing a particular order component of a prescription order may differ from the steps required for another order component of a prescription order. It may be useful to hold, accumulate or otherwise consolidate one or more order components of a prescription order while one or more other order components of the prescription order are prepared, undergo quality control, or otherwise reviewed or processed at a high volume pharmacy. An accumulation device may be deployed to facilitate accumulation or consolidation of one or more order components of a prescription order.

Figure 1:
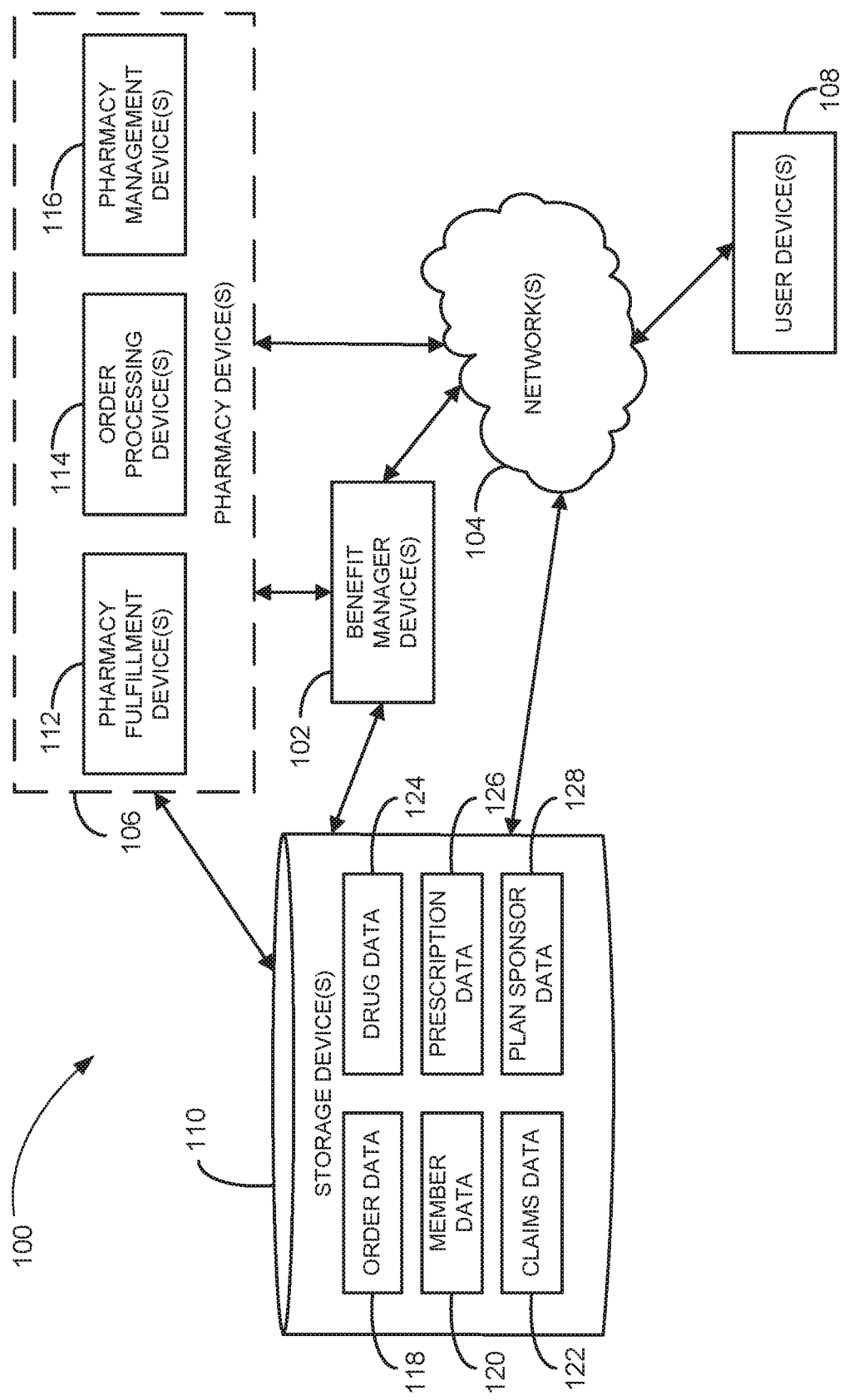
FIG. 1 is a block diagram of an example system, according to an example embodiment.

FIG. 1 is a block diagram of an example implementation of a system 100, according to an example embodiment. While the system 100 is generally described as being deployed in a high volume pharmacy or fulfillment center (e.g., a mail order pharmacy, a direct delivery pharmacy, an automated pharmacy, multiple package delivery center, and the like), the system 100 and/or components thereof may otherwise be deployed (e.g., in a lower volume pharmacy).

A high volume pharmacy may be a pharmacy that is capable of filling prescriptions automatically, mechanically, manually, or a combination thereof. The system 100 may include a benefit manager device 102, a pharmacy device 106, and a user device 108, which may communicate with each other directly and/or over a network 104. The system 100 may also include a storage device 110.

The benefit manager device 102 is a device operated by an entity that is at least partially responsible for creation and/or management of the pharmacy or drug benefit. While such an entity operating the benefit manager device 102 is typically a pharmacy benefit manager (PBM), other entities may operate the benefit manager device 102 either on behalf of themselves, the PBM, another entity, or other entities. For example, the benefit manager device 102 may be operated by a health plan, a retail pharmacy chain, a drug wholesaler, a data analytics or other type of software-related company, or the like. In some embodiments, a PBM that provides the pharmacy benefit may also provide one or more than one additional benefits including a medical or health benefit, a dental benefit, a vision benefit, a wellness benefit, a radiology benefit, a pet care benefit, an insurance benefit, a long term care benefit, a nursing home benefit, and the like. The PBM may, in addition to its PBM operations, operate one or more than one pharmacy. The pharmacies may be retail pharmacies, mail order pharmacies, specialty pharmacies, pharmaceutical vending machines or kiosks, and the like.

Some of the operations of the PBM that operates the benefit manager device 102 may include the following activities and processes. A member (or a person on behalf of the member) of a pharmacy benefit plan administered by or through the PBM attempts to obtain a prescription drug at a retail pharmacy location (e.g., a location of a physical store) from a pharmacist or a pharmacist technician. The member may also attempt to obtain the prescription drug through mail order drug delivery from a mail order pharmacy location, which may be the high volume pharmacy system 100. In some embodiments, the member may also attempt to obtain the prescription drug directly or indirectly through the use of a machine, such as a kiosk, vending unit, mobile electronic device, or a different type of mechanical, electrical, electronic communication device, and/or computing device. Such a machine may be filled with the prescription drug in prescription packaging, which may include multiple prescription components, by the high volume pharmacy system 100.

The member may have a copayment for the prescription drug that reflects an amount of money that the member is responsible to pay the pharmacy for the prescription drug. The money paid by the member to the pharmacy may come from personal funds of the member, a health savings account (HSA) of the member or the member's family, a health reimbursement arrangement (HRA) of the member or the member's family, a flexible spending account (FSA) of the member or the member's family, or the like. In some instances, an employer of the member may directly or indirectly fund or reimburse the member for the copayments.

The amount of the co-pay required from the member may vary with different pharmacy benefit plans having different plan sponsors or clients and/or prescription drugs. The member's copayment may be based on a flat copayment (e.g., $10 or other dollar amounts), co-insurance (e.g., 10% or other percents), and/or a deductible (e.g., for first $500 of annual prescription drug expenses or other dollar amounts) for certain prescription drugs, certain types and/or classes of prescription drugs, and/or all prescription drugs. The copayment may be stored in the storage 110 or determined by the benefit manager device 102.

In some instances, the member may not pay the copayment or may only pay a portion of the copayment for the prescription drug. For example, if the usual and customary cost for a generic version of a prescription drug is $4, and the member's flat copayment is $20 for the prescription drug, the member may only be required to pay $4 to receive the prescription drug. In another example involving a worker's compensation claim, no copayment may be due by the member for the prescription drug.

In addition, copayments may also vary based on different delivery channels used for the prescription drug to be received by the member. For example, the copayment for receiving the prescription drug from a mail order pharmacy location may be less than the copayment for receiving the prescription drug from a retail pharmacy location.

In conjunction with receiving the copayment (if any) from the member and dispensing the prescription drug to the member, the pharmacy submits a claim to the PBM for the prescription drug. After receiving the PBM (e.g., through the benefit manager device 102) may perform certain adjudication operations including verifying eligibility for the member, identifying and/or reviewing an applicable formulary for the member to determine any appropriate copayment, coinsurance, and deductible for the prescription drug, and performing a drug utilization review (DUR) on the member. The PBM provides a response to the pharmacy (e.g. from the benefit manager device 102 to the pharmacy device 106) following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated.

The aforementioned adjudication operations generally occur before the copayment is received and the prescription drug is dispensed. However, in some instances these operations may occur simultaneously, substantially simultaneously, or in a different order. In addition, more or less adjudication operations may be performed as at least part of the adjudication process.

The amount of reimbursement paid to the pharmacy by a plan sponsor and/or money paid by the member may be determined at least partially based on the type(s) of pharmacy network in which the pharmacy is included. Other factors may also be used to determine the amount in addition to the type of pharmacy network. For example, if the member pays the pharmacy for the prescription drug without using the prescription drug benefit provided by the PBM (e.g., by paying cash without use of the prescription drug benefit or by use of a so-called pharmacy discount card offering other negotiated rates), the amount of money paid by the member may be different than when the member uses the prescription or drug benefit. In some embodiments, the amount of money received by the pharmacy for dispensing the prescription drug and for the prescription drug itself may be higher than when the member uses the prescription or drug benefit. Some or all of the foregoing operations may be performed by executing instructions stored on the benefit manager device 102 and/or an additional device.

Examples of the network 104 include Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. The network 104 may include an optical network. The network 104 may be a local area network or a global communication network, such as the Internet. In some embodiments, the network 104 may include a network dedicated to prescription orders, e.g., a prescribing network such as the electronic prescribing network operated by Surescripts of Arlington, Va.

Moreover, although the system shows a single network 104, multiple networks can be used. The multiple networks may communicate in series with each other to link the devices 102, 106-110 or in parallel to link the devices 102, 106-110.

The pharmacy device 106 may include an order processing device 114, a pharmacy management device 116, and a pharmacy fulfillment device 112 in communication with each other directly and/or over the network 104.

The order processing device 114 may receive information regarding filling prescriptions and may direct an order component to one or more than one of the devices of the pharmacy fulfillment device 112 at a pharmacy. The pharmacy fulfillment device 112 may fulfill, dispense, aggregate, and/or pack the order components of the prescription drugs in accordance with one or more than one of the prescription orders directed by the order processing device 114. The order processing device 114 may be deployed in the system 100, or may otherwise be used.

In general, the order processing device 114 is a device located within or otherwise associated with the pharmacy to enable fulfillment of a prescription and dispensing prescription drugs by the pharmacy fulfilment device 112. In some embodiments, the order processing device 114 may be an external device separate from the pharmacy and communicate with other devices located within the pharmacy.

For example, the external order processing device 114 may communicate with an internal order processing device 114 and/or other devices located within the system 100. In some embodiments, the external order processing device 114 may have limited functionality (e.g., as operated by a patient requesting fulfillment of a prescription drug), while the internal pharmacy order processing device 114 may have greater functionality (e.g., as operated by a pharmacist).

The order processing device 114 may track the prescription order as it is fulfilled by the pharmacy fulfillment device 112. The prescription order may include one or more than one prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a patient or a patient family. The order processing device 114 may also track and/or schedule literature or paperwork associated with each prescription order or multiple prescription orders that are being shipped together.

The pharmacy management device 116 may enable and/or facilitate management and operations in a pharmacy. For example, the pharmacy management device 116 may provide functionality to enable receipt and processing of prescription drug claims, management of pharmacy personnel, management of pharmaceutical and non-pharmaceutical products, track products in the pharmacy, record workplace incidents involve personnel and products, and the like. In some embodiments, the order processing device 114 may operate in combination with the pharmacy management device 116.

In some embodiments, the pharmacy management device 116 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy management device 116 may be utilized by the pharmacy to submit the claim to the PBM (e.g., through the benefit management device 102) for adjudication.

In some embodiments, the pharmacy management device 116 may enable information exchange between the pharmacy and the PBM, for example, to allow the sharing of member information such as drug history, and the like, that may allow the pharmacy to better service a member (e.g., by providing more informed therapy consultation and drug interaction information, etc.). In some embodiments, the benefit manager 102 may track prescription drug fulfillment and/or other information for patients that are not members or have not identified themselves as members, at the time (or in conjunction with the time) in which they seek to have a prescription filled at a pharmacy.

The pharmacy fulfillment devices 112, the order processing device 114, and/or the pharmacy management device 116 may include circuitry, a processor, a memory to store data and instructions, and communication functionality. These devices 112-116, in some embodiments, are dedicated to performing processes, methods and/or instructions described herein. Other types of electronic devices specifically configured to implement with the processes, methods and/or instructions described herein may also be used.

In some embodiments, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (e.g., by utilizing a local storage) and/or through the network 104 (e.g., by utilizing a cloud configuration or software as a service. etc.) with the storage 110.

The user device 108 is used by a device operator. The device operator may be a user (e.g., an employee, a contractor, a benefit member, a patient of the pharmacy, or the like) associated with the system 100. Other device operators may also operate the user device 108. In some embodiments, the user device 108 may enable the device operator to attend to pharmacy operations in a convenient manner (e.g., remote from a pharmacy). In some embodiments, the user device 108 may enable the device operator to receive information about pharmacy processes, prescription drug fulfillment status, and the like.

The user device 108 may be a stand-alone device that solely provides at least some of the functionality of the methods and systems, or may be a multi-use device that has functionality outside of analysis of the methods and systems. Examples of the user device 108 include a set-top box (STB), a receiver card, a mobile telephone, a personal digital assistant (PDA), a display device, a portable gaming unit, a computing system, and the like. Other devices, however, may also be used. In some embodiments, the computing system may include a mobile computing device. For example, the user device 108 may include a mobile electronic device, such an iPhone or iPad by Apple, Inc., mobile electronic devices powered by Android by Google, Inc., and a Blackberry by Research In Motion Limited. The user device 108 may also include other computing devices, such as desktop computing devices, notebook computing devices, netbook computing devices, gaming devices, and the like. Other types of electronic devices may also be used.

The storage device 110 may include: a non-transitory storage (e.g., memory, hard disk, CD-ROM, and the like) in communication with the benefit manager device 102, the pharmacy device 106, and/or the user device 108 directly and/or over the network 104. The non-transitory storage may store order data 118, member 120, claims data 122, drug data 124, prescription data 126, and/or plan sponsor 128. Further, the system 100 may include additional devices, which may communicate with each other directly or over the network 104.

The order data 118 may be related to a prescription order. The order data may include the type of the prescription drug (e.g., drug name and strength) and quantity of the prescription drug. The order data 118 may also include data used for completion of the prescription, such as prescription materials and/or the type and/or size of container in which the drug is dispensed or in which is requested to be dispensed. In general, prescription materials include an electronic copy of information regarding the prescription drug for inclusion with or otherwise provided (e.g., via email) in conjunction with the fulfilled prescription. The prescription materials may include electronic information regarding drug interaction warnings, recommended usage, possible side effects, expiration date, date of prescribing, or the like. The order data 118 may be used by the pharmacy to fulfill a pharmacy order.

In some embodiments, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (e.g., a prescription bottle and sealing lid, prescription packaging, and the like) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other type of verification information such as bar code data read from pallets, bins, trays, carts, and the like used to facilitate transportation of prescriptions within the pharmacy may also be stored as order data 118.

The member data 120 includes information regarding the members associated with the PBM. The information stored as member data 120 may include personal information, personal health information, protected health information, fitness data, health data, web and mobile app activity, and the like. Examples of the member data 120 include name, address, telephone number, e-mail address, prescription drug history, and the like. The member data 120 may include a plan sponsor identifier that identifies the plan sponsor associated with the member and/or a member identifier that identifies the member to the plan sponsor. The member data 120 may also include, by way of example, dispensation preferences such as type of label, type of cap, message preferences, language preferences, or the like.

The member data 120 may be accessed by various devices in the pharmacy to obtain information utilized for fulfillment and shipping of prescription orders. In some embodiments, an external order processing device 114 operated by or on behalf of a member may have access to at least a portion of the member data 120 for review, verification, or other purposes.

In some embodiments, the member data 120 may include information for persons who are patients of the pharmacy but are not members in a pharmacy benefit plan being provided by PBM. For example, these patients may obtain drug directly from the pharmacy, through a private label service offered by the pharmacy, or otherwise. In general, the use of the terms member (e.g., of a prescription drug benefit plan) and patient (e.g., of a pharmacy) may be used interchangeably in this disclosure.

The claims data 122 includes information regarding pharmacy claims adjudicated by the PBM under a drug benefit program provided by the PBM for one, or more than one, plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number), the dispensing date, generic indicator, GPI number, medication class, the cost of the prescription drug provided under the drug benefit program, the copay/coinsurance amount, rebate information, and/or member eligibility, and the like. Additional information may be included.

In some embodiments, other types of claims beyond prescription drug claims may be stored in the claims data 122. For example, medical claims, dental claims, wellness claims, or other type of health care-related claims for members may be stored as a portion of the claims data 122.

In some embodiments, the claims data 122 includes claims that identify the members with whom the claims are associated. In some embodiments, the claims data 122 includes claims that have been de-identified (e.g., associated with a unique identifier but not with a particular, identifiable member), aggregated, and/or otherwise processed.

The drug data 124 may include drug name (e.g., technical name and/or common name), other names by which the drug is known by, active ingredients, an image of the drug (e.g., in pill form), and the like. The drug data 124 may include information associated with a single medication or multiple medications.

The prescription data 126 may include information regarding prescriptions that may be issued by prescribers on behalf of patients, who may be members of the pharmacy benefit plan, for example to be filled by a pharmacy. Examples of the prescription data 126 include patient names, medication or treatment (such as lab tests), dosing information, and the like. The prescriptions may be electronic prescriptions, paper prescriptions that have been scanned, or otherwise. In some embodiments, the dosing information reflects a frequency of use (e.g., once a day, twice a day, before each meal, etc.) and a duration of use (e.g., a few days, a week, a few weeks, a month, etc.).

In some embodiments, the order data 118 may be linked to associated member data 120, claims data 122, drug data 124, and/or prescription data 126.

The plan sponsor data 128 includes information regarding the plan sponsors of the PBM. Examples of the plan sponsor data 128 include company name, company address, contact name, contact telephone number, contact e-mail address, and the like.

Figure 2:
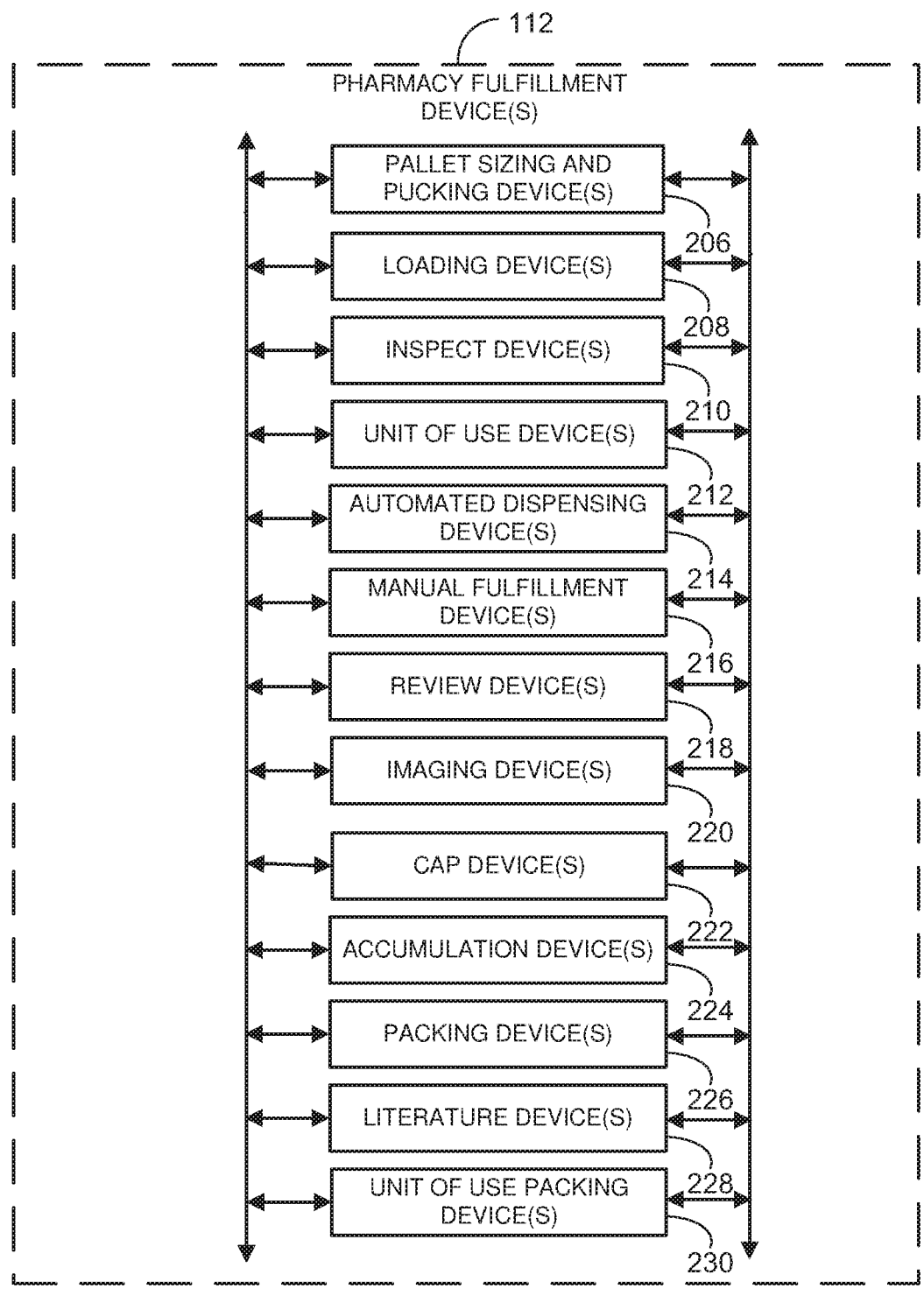
FIG. 2 is a block diagram of an example order processing device that may be deployed within the system of FIG. 1, according to an example embodiment.

FIG. 2 illustrates the pharmacy fulfillment device 112, according to an example embodiment. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device 102, the order processing device 114, and/or the non-transitory storage 110, directly or over the network 104. Specifically, the pharmacy fulfillment device 112 may include pallet sizing and pucking device(s) 206; loading device(s) 208; inspect device(s) 210, unit of use device(s) 212, automated dispensing device(s) 214, manual fulfillment device(s) 214, review device(s) 218, imaging device(s) 220, cap device(s) 222, accumulation device(s) 224, literature device(s) 228, packing device(s) 226, and unit of use packing device(s) 230. Further, the pharmacy fulfillment device 112 may include additional devices, which may communicate with each other directly or over the network 104.

In some embodiments, operations performed by one or more of these devices 206-230 may be performed sequentially, or in parallel with the operations of devices as may be coordinated by the order processing device 114. In some embodiments, the order processing device 114 tracks a prescription with the pharmacy based on operations performed by one or more than one of the devices 206-230.

In some embodiments, the pharmacy fulfillment device 112 may transport prescription drug containers, for example, between more than one of the devices 206-230 in the high volume fulfillment center, by use of pallets. The pallet sizing and pucking device 206 may configure pucks in a pallet. A pallet may be a transport structure for a number of prescription containers, and may include a number of cavities. A puck may be placed in one or more than one of the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism, or the like. In one embodiment, the loading device 208 has robotic arms or pickers to grasp a prescription container and move it to and from a pallet or to and from a puck. The loading device 208 may also print a label that is appropriate for a container that is to be loaded onto the pallet, and apply the label to the container. The pallet may be located on a conveyor assembly during these operations (e.g., at the high volume fulfillment center or the like).

The inspect device 210 may verify that containers in a pallet are correctly labeled and in the correct spot on the pallet. The inspect device 210 may scan the label on one or more than one container on the pallet. Labels of containers may be scanned or imaged in full or in part by the inspect device 210. Such imaging may occur after the container has been lifted out of its puck by a robotic arm, picker, or the like, or may be otherwise scanned or imaged while retained in the puck. In some embodiments, images and/or video captured by the inspect device 210 may be stored in the storage device 110 as a portion of the order data 118.

The unit of use device 212 may temporarily store, monitor, label and/or dispense unit of use products. In general, unit of use products are prescription drug products that may be delivered to a patient or member without being repackaged at the pharmacy. These products may include pills in a container, pills in a blister pack, inhalers, liquids in a spray or other dispensing container, and the like. Prescription drug products dispensed by the unit of use device 212 may be packaged individually or collectively for shipping, or may be shipped in combination with other prescription drugs dispensed by other devices (e.g., in the high volume fulfillment center).

At least some of the operations of devices 206-230 may be directed by the order processing device 114. For example, the manual fulfillment device 216, the review device 218, the automated dispensing device 214, the packing device 226, and/or another device may receive instructions provided by the order processing device 114.

The automated dispensing device 214 may include one or more than one devices that dispense prescription drugs or pharmaceuticals into prescription containers in accordance with one or multiple prescription orders. In general, the automated dispensing device 214 may include mechanical and electronic components with, in some embodiments, software and/or logic to facilitate pharmaceutical dispensing that would otherwise be performed in a manual fashion by a pharmacist and/or pharmacist technician. For example, the automated dispensing device 214 may include high volume fillers that fill a number of prescription drug types at a rapid rate and blister pack machines that dispense and pack drugs into a blister pack. Prescription drugs dispensed by the automated dispensing devices 214 may be packaged individually or collectively for shipping, or may be shipped in combination with other prescription drugs dispensed by other devices in the high volume fulfillment center.

The manual fulfillment device 216 may provide for manual fulfillment of prescriptions. For example, the manual fulfillment device 216 may receive or obtain a container and enable fulfillment of the container by a pharmacist or pharmacy technician. In some embodiments, the manual fulfillment device 216 provides the filled container to another device in the pharmacy fulfillment devices 112 to be joined with other containers in a prescription order for a patient or member. In general, a manual fulfillment may include operations at least partially performed by a pharmacist or a pharmacy technician. For example, a person may retrieve a supply of the prescribed drug, may make an observation, may count out a prescribed quantity of drugs and place them into a prescription container, or the like. Some portions of the manual fulfillment process may be automated by use of a machine. For example, counting of capsules, tablets, or pills may be at least partially automated (e.g., through use of a pill counter or the like). Prescription drugs dispensed by the manual fulfillment device 216 may be packaged individually or collectively for shipping, or may be shipped in combination with other prescription drugs dispensed by other devices in the high volume fulfillment center.

The review device 218 may process prescription containers to be reviewed by a pharmacist for proper pill count, exception handling, prescription verification, and the like. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been cancelled, containers with defects, and the like. In an example embodiment, the manual review may be performed at the manual station.

The imaging device 220 may image containers prior to filling and/or after they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114, and/or stored in the storage device 110 as part of the order data 118.

The cap device 222 may be used to cap or otherwise seal a prescription container. In some embodiments, the cap device 222 may secure a prescription container with a type of cap in accordance with a patient preference (e.g., a preference regarding child resistance, a preference regarding built-in adherence functionality, or the like), a plan sponsor preference, a prescriber preference, or the like. The cap device 222 may also etch a message into the cap or otherwise associate a message into the cap, although this process may be performed by a different device in the high volume fulfillment center.

The accumulation device 224 accumulates various containers of prescription drugs in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218, at the high volume fulfillment center. The accumulation device 224 may be used to group the prescription containers prior to shipment to the member or otherwise.

The literature device 228 prints, or otherwise generates, literature to include with prescription drug orders. The literature may be printed on multiple sheets of substrates, such as paper, coated paper, printable polymers, or combinations thereof. The literature printed by the literature device 228 may include information required to accompany the prescription drugs included in a prescription order, relating to prescription drugs in the order, financial information associated with the order (e.g., an invoice or an account statement, or the like).

In some embodiments, the literature device 228 folds or otherwise prepares the literature for inclusion with a prescription drug order (e.g., in a shipping container or the like). In some embodiments, the literature device 228 that prints the literature may be separate from the literature device that prepares the literature for inclusion with a prescription order.

The packing device 226 packages a prescription order in preparation for shipping the order. The packing device 226 may box, bag, or otherwise package the fulfilled prescription order for delivery. The packing device 226 may further place inserts, (e.g., literature or other papers), into the packaging received from the literature device 228 or otherwise. For example, bulk prescription orders may be shipped in a box, while other prescription orders may be shipped in a bag which may be a wrap seal bag. The packing device 226 may label the box or bag with an address and a recipient's name. The label may be printed and affixed to the bag or box, be printed directly onto the bag or box, or otherwise associated with the bag or box. The packing device 226 may sort the box or bag for mailing in an efficient manner (e.g., sort by delivery address, sort by zip code, or the like). The packing device 226 may include ice or temperature sensitive elements for prescriptions which are to be kept within a temperature range during shipping in order to retain efficacy or otherwise. The ultimate package may then be shipped through postal mail, through a mail order delivery service that ships via ground and/or air (e.g., UPS, FEDEX, or DHL, or the like), through delivery service, through a local delivery service (e.g., a courier service), through a locker box at a shipping site (e.g., an AMAZON locker, library locker, a post office box, or the like), or otherwise.

The unit of use packing device 230 packages a unit of use prescription order in preparation for shipping the order. The unit of use packing device 230 may include manual scanning of containers to be bagged for shipping to verify each container in the order. In an example embodiment, the manual scanning may be performed at a manual station.

The pharmacy fulfillment device 112 in FIG. may include single devices 206-230 or multiple devices 206-230 (e.g., depending upon implementation in a pharmacy). The devices 206-230 may be the same type or model of device or may be different device types or models. When multiple devices are present, the multiple devices may be of the same device type or models or may be a different device type or model. The types of devices 206-230 shown in FIG. 2 are example devices. In other configurations of the system 100, lesser, additional, or different types of devices may be included.

Moreover, multiple devices may share processing and/or memory resources. The devices 206-230 may be located in the same area or in different locations. For example, the devices 206-230 may be located in a building or set of adjoining buildings. The devices 206-230 may be interconnected (e.g., by conveyors), networked, and/or otherwise in contact with one another or integrated with one another (e.g., at the high volume fulfillment center). In addition, the functionality of a device may be split among a number of discrete devices and/or combined with other devices.

Figure 3:
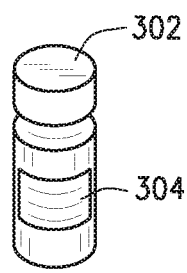
FIG. 3 is a perspective of a bottle that may be used in the system of FIG. 1, according to an example embodiment.

FIG. 3 illustrates a bottle 302 that may be utilized by a pharmacy for fulfillment of a prescription order and that may be accumulated by the accumulation device 224. The bottle 302 is generally cylindrical with an open interior and may be of one or a variety of sizes utilized by a pharmacy for fulfillment of a prescription. For example, a pharmacy may have two different sized bottles or three different sized bottles. Any number of different sized bottles 302 may be used. Different sized bottles may be further described, for example, as having differing volumes, differing diameters, and/or differing heights. Shapes other than cylindrical shapes may be used for the bottles 302. Examples of other shapes include regular prisms, elliptical cylinders, and combinations thereof. The bottles 302 may include labels 304. A label 304 may be uniquely printed for each bottle 302 (e.g., to include information such as a patient name, drug name, dosage, directions for use, and/or other information required and/or desirable for a prescription label). The labels 304, or some portion of the information for the labels 304, may be the same for a particular set of the labels 304, such as the dispensing pharmacy. Although the accumulation device 224 is generally described as being utilized to accumulate bottles, in some embodiments, other suitable containers may be accumulated by an accumulation device 224.

Figure 4:
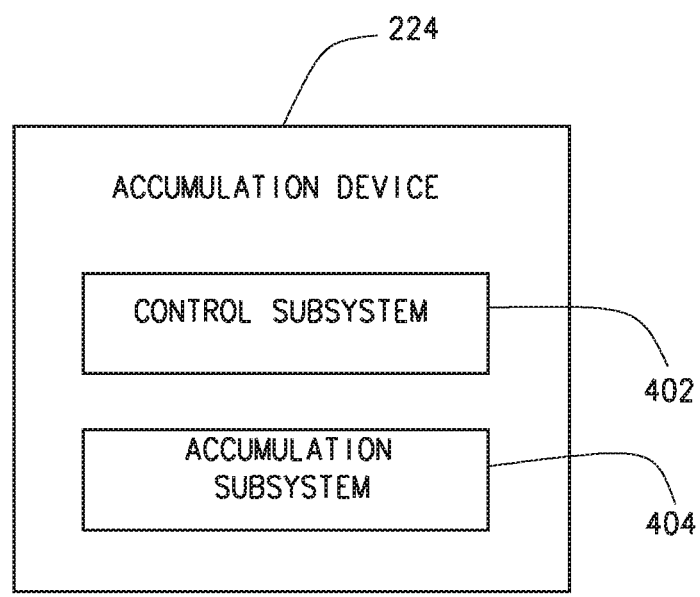
FIG. 4 is a block diagram of an accumulation device that may be deployed within the system of FIG. 1, according to an example embodiment.
Figure 5:
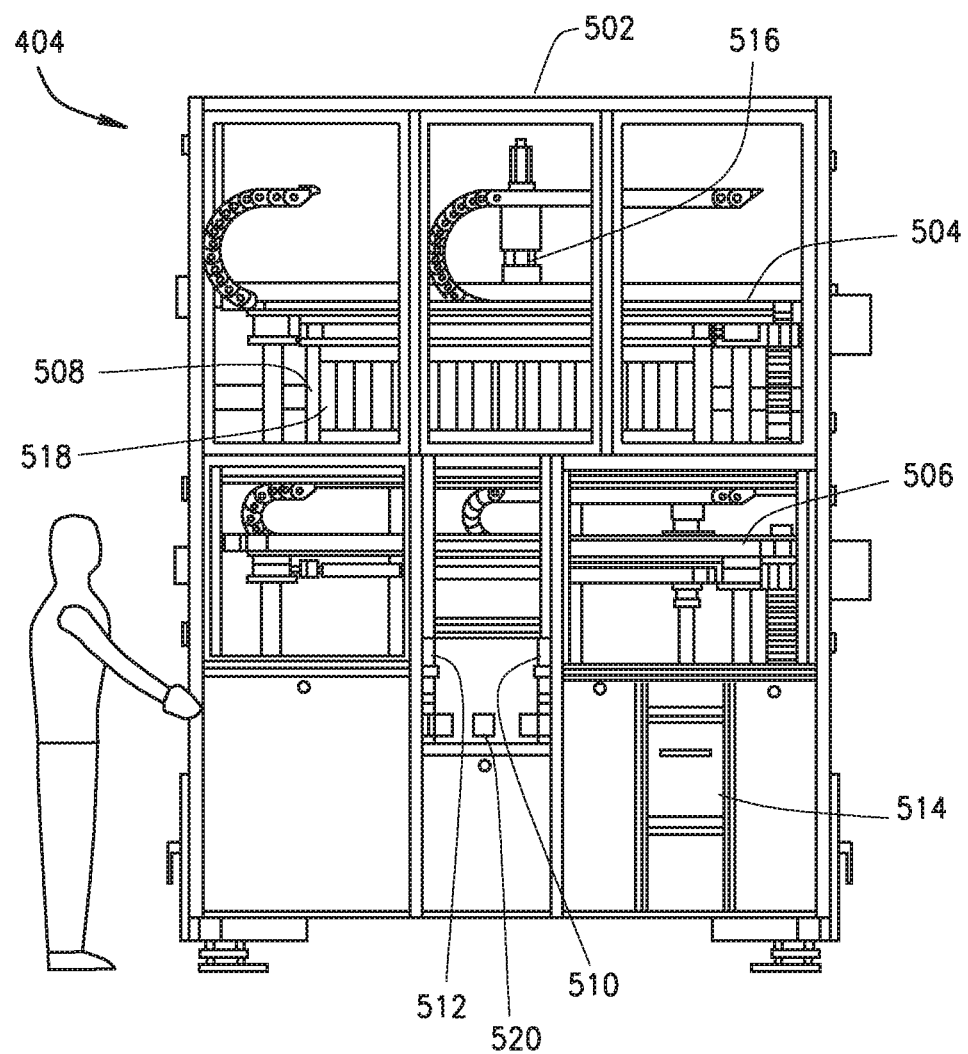
FIG. 5 is an end view of the accumulation subsystem of the accumulation device of FIG. 4, according to an example embodiment.
Figure 6:
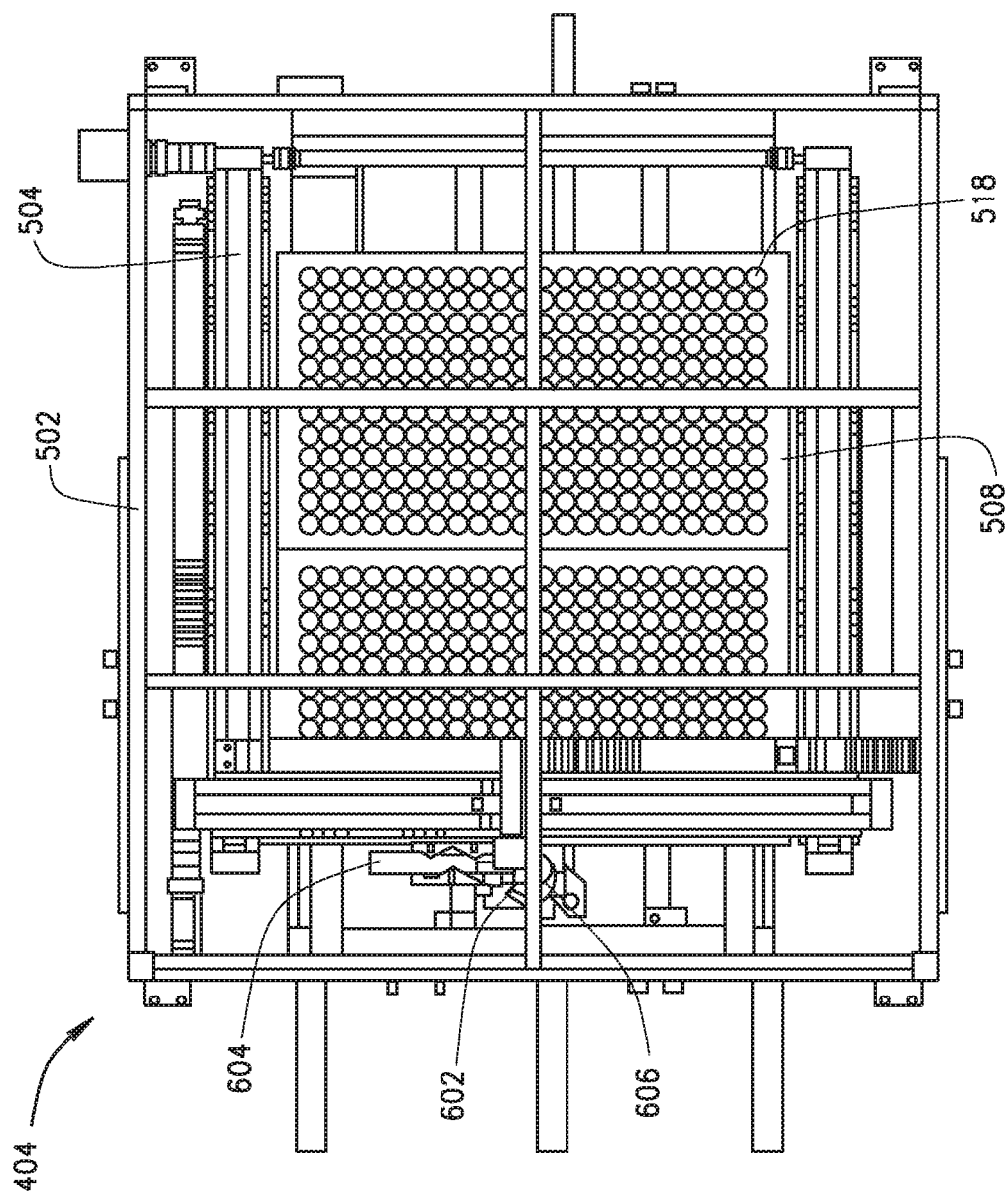
FIG. 6 is a top view of the accumulation subsystem of FIG. 5, according to an example embodiment.
Figure 7:
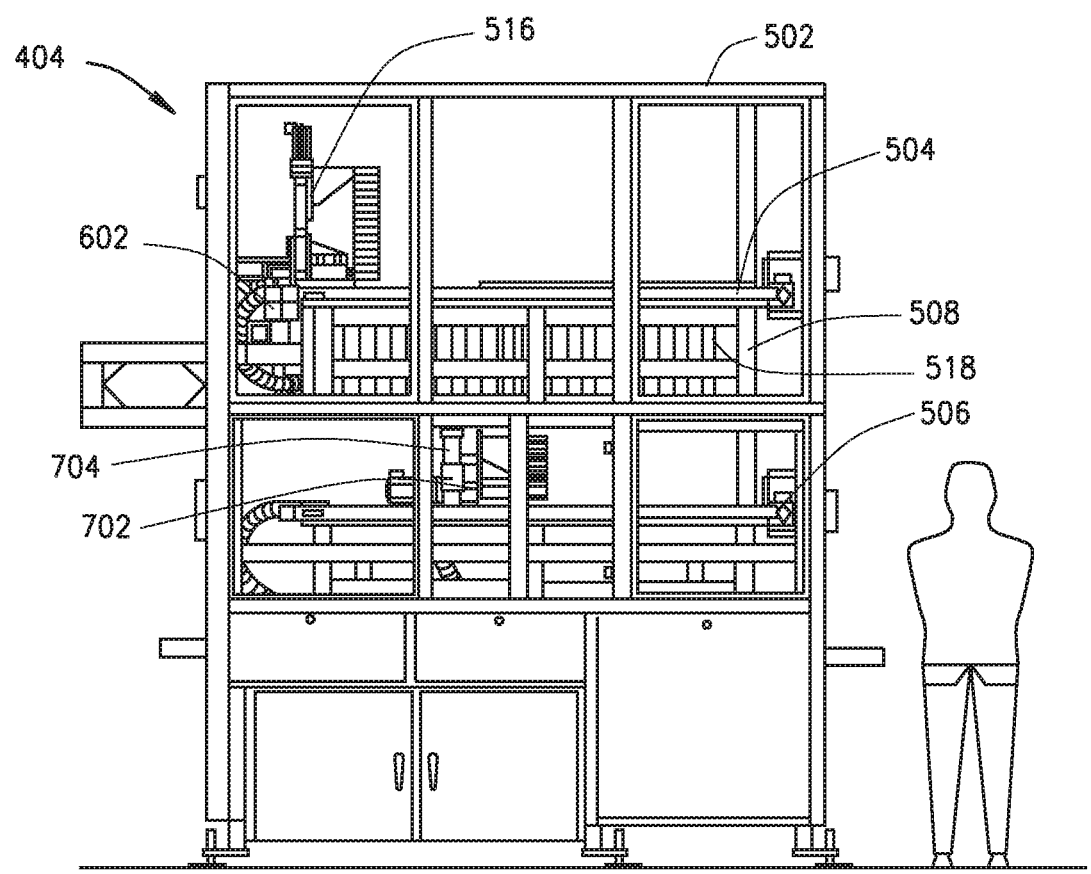
FIG. 7 is a side view of the accumulation subsystem of FIG. 5, according to an example embodiment.
Figure 8:
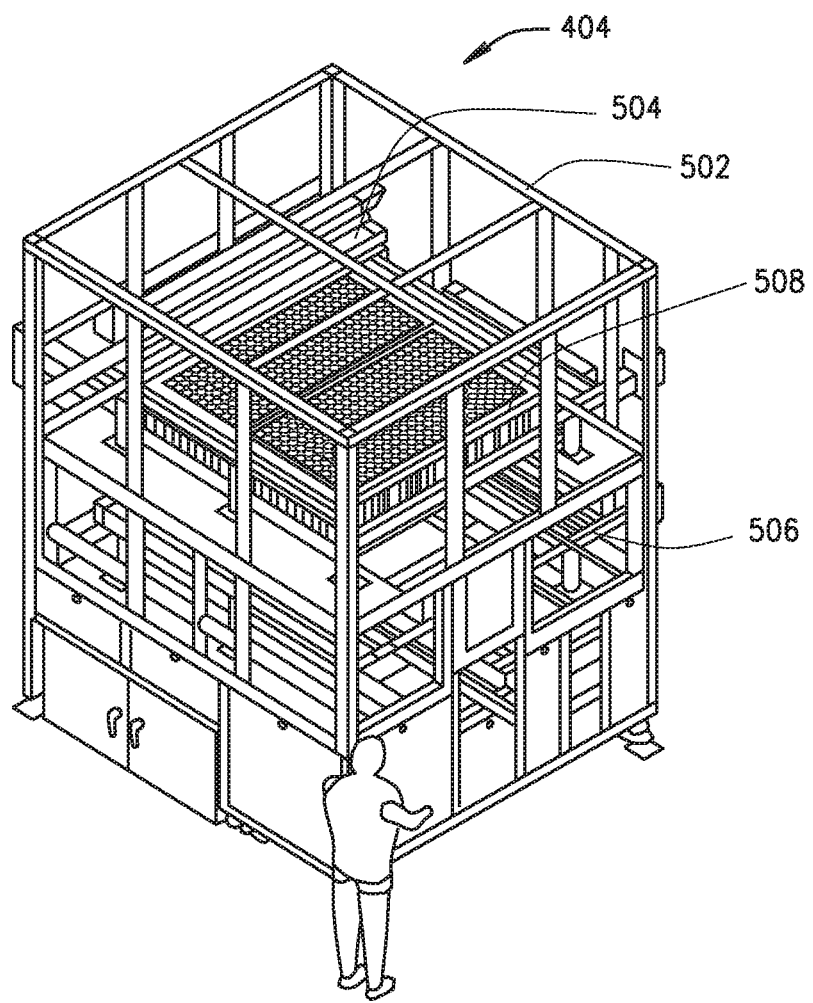
FIG. 8 is a perspective view of the accumulation subsystem of FIG. 5, according to an example embodiment.

FIG. 4 illustrates an accumulation device 224, according to an example embodiment. The accumulation device 224 may be deployed in the system 100 of FIG. 1, or may otherwise be used. The accumulation device 224 may include a control subsystem 402 and an accumulation subsystem 404. The control subsystem 402 may include a single module or multiple modules and enables the automated dispensing device 214 to control the accumulation subsystem 404, while the accumulation subsystem 404 may include a single or multiple devices and enables the accumulation device 224 with accumulation operations (e.g., accumulating containers of prescription drugs in an individual prescription order).

An example deployment of the accumulation device 224 is within the system 100. In such a deployment, the system 100 includes a single conveyor or multiple conveyors, robotic transport systems or other devices to facilitate transporting containers or pallets of containers 302 through mechanical devices within the system 100, such as devices to label, fill, cap, and check containers. The accumulation device 224 may be otherwise deployed.

The accumulation device 224 may be deployed to accumulate multiple prescription bottles 302 in a prescription order. One or more of the steps of labeling, filling, capping or checking one or more of the bottles 302 in the prescription order may be delayed relative to one or more than one of the steps of labeling, filling, capping or checking for another one or more of the containers in the same prescription order. The accumulation device 224 may store the bottles 302 while other containers are processed. The accumulation device 224 may be deployed to reintroduce a prescription bottle 302 into a portion of the system 100, e.g., via one or more conveyors, which is in communication with devices configured to pack and ship the prescription order that is or includes the prescription bottle 302. Devices configured to pack and ship the prescription order may include the packing device(s) 226, 230. For example, a prescription container 302 reviewed pursuant to quality assurance processes (e.g., using the review device 218) may be transported to the accumulation subsystem 404 of the accumulation device 224 for further processing. The accumulation device 224 may be deployed to retain one or more than one prescription bottle 302 of a prescription order until other components of the prescription order, such as prescription drug products dispensed by the unit of use device 230, the automated dispensing device 214, and/or the manual fulfillment device 216 have been selected or prepared for the prescription order. In an example embodiment, the accumulation device 224 is deployed for at least all of the foregoing purposes. In another example embodiment, the accumulation device 224 is deployed for fewer than all of the foregoing purposes. In yet another example embodiment, the accumulation device 224 is deployed to retain one or more than one bottle 302 of a prescription order during any period in which there is not a complete path through the system 100 to package and ship the entire prescription order. In another embodiment, the accumulation device 224 is deployed to retain one or more than one bottle 302 of a prescription order while another order component is reviewed for quality assurance or prescription verification purposes, either at a review device 218 or otherwise within the system 100.

FIGS. 5-8 illustrate the accumulation subsystem 404, according to an example embodiment. The accumulation subsystem 404 may be deployed within the accumulation device 224, or may otherwise be deployed. The accumulation subsystem 404 enables accumulation of multiple bottles 302 of prescription drugs in an automatic or semiautomatic manner. For example, the accumulation subsystem 404 may accumulate prescription bottles 302 from any one or more of the unit of use device 210, the automated dispensing device 212, the manual fulfillment device 216, and the review device 218. The accumulation subsystem 404 may accumulate one or more prescription bottles 302 for subsequent quality assurance validation or prescription verification or validation, or while one or more other order component of the prescription order is undergoing quality assurance validation or prescription verification or validation. The accumulation subsystem 404 may accumulate multiple prescription bottles 302 from a single device, such as the manual fulfillment device 216 or the review device 218. In reference to a particular prescription order, the accumulation subsystem 404 may accumulate multiple prescription bottles 302 corresponding to that prescription order within the accumulation subsystem 404. In some embodiments, the accumulation subsystem 404 may temporarily store a single or multiple prescription bottles 302 corresponding to that prescription order during all or a portion of a period in which other portions of that prescription order are being fulfilled, checked, or otherwise processed elsewhere in the system 100, for example, by the unit of use device 212.

The accumulation subsystem 404 illustrated in FIGS. 5-8 includes a frame 502, a bottle scan and pick assembly 602, an upper gantry 504, a lower gantry 506, a table assembly 508, a bottle escapement assembly 510, 512 and a reject bin assembly 514.

The frame 502 provides support for one or more devices of the accumulation subsystem 404, such as a bottle scan and pick assembly 602, an upper gantry 504, a lower gantry 506, a table assembly 508, bottle escapement assemblies 510, 512, and a reject bin assembly 514. Although two bottle escapement assemblies 510, 512 are illustrated in the embodiment of the accumulation subsystem 404 of FIG. 5, in other embodiments, the accumulation subsystem 404 may have only one bottle escapement assembly or may have more than two bottle escapement assemblies.

The bottles 302 may be transported to the bottle scan and pick assembly 602 via an entry conveyor 604. The entry conveyor 604 may be a belt conveyor or a chain conveyor; however, other types of conveyors may be used for the entry conveyor 604. As described in further detail below, the bottle scan and pick assembly 602 may include a rotary assembly 606 configured to receive bottles 302. The rotary assembly 606 may rotate to place the bottles 302 in a pick position. The bottle scan and pick assembly 602 may include a gripper assembly 516 that is configured to grip the bottle 302 in the pick position.

The gripper assembly 516 may be in communication with the upper gantry 504. The upper gantry 504 may facilitate movement of the gripper assembly 516 along x, y and z axis above the table assembly 508. In an example embodiment, the upper gantry 504 is or includes x, y and z Bosch linear actuators. Other embodiments of gantries may be deployed as the upper gantry 504 in the accumulation subsystem 404.

The table assembly 508 includes multiple holding tubes configured to receive bottles 302, such as holding tube 518. The upper gantry 504, in combination with the gripper assembly 516, may be deployed to select the bottle 302 from the pick position of the rotary assembly 606, lift the bottle 302 out of the rotary assembly 606, move the bottle to a position over a holding tube, such as the holding tube 518, and release the bottle into the holding tube 518. It should be appreciated that in another embodiment of a table assembly, in lieu of holding tubes, a number of rods could be deployed to form points of points of contact around the perimeter of a bottle to retain bottles within the table. The rods could be otherwise configured to perform the functions of the holding tubes, as described herein.

The lower gantry 506 facilitates movement of an unload assembly 702 along x, y and z axis beneath the holding tubes, such as holding tube 518, of the table assembly 508 and over the bottle escapement assemblies 510, 512. In an example embodiment, the lower gantry 506 is or includes x, y and z Bosch linear actuators. Other embodiments of gantries may be deployed as the lower gantry 506 in the accumulation subsystem 404. The lower gantry 506 is described in further detail below.

As described in further detail below, the unload assembly 702 may be configured to release bottles 302 from the holding tube 518 such that the bottle(s) 302 held in the holding tube 518 are received by an unload assembly tube 704. The unload assembly 702 may be further configured to empty bottle(s) 302 from the unload assembly tube 704 into the bottle escapement assemblies 510, 512.

The accumulated or temporarily stored bottle(s) 302 deposited into the bottle escapement assemblies 510, 512 may pass through and exit the bottle escapement assemblies 510, 512, onto exit conveyor 520. The exit conveyor 520 may transport the accumulated bottles 302 out of the accumulation system 304 to other devices within the system 100, for example to the literature device(s) 228 or the packing device(s) 226, 230.

Figure 9:
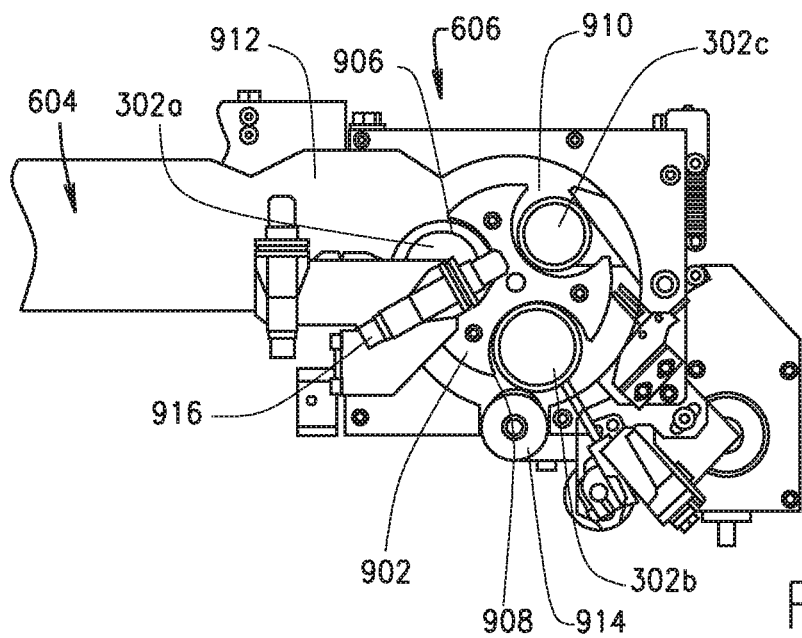
FIG. 9 is a detailed top view of a rotary assembly that may be deployed within the accumulation subsystem of FIG. 5, according to an example embodiment.
Figure 10:
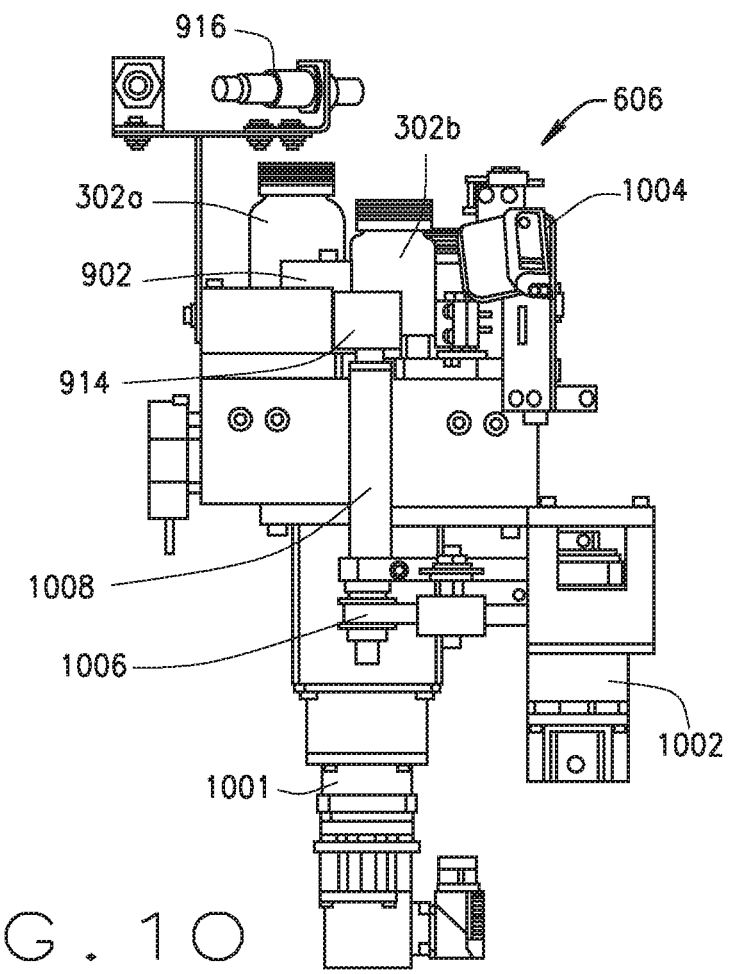
FIG. 10 is a side view of the rotary assembly of FIG. 9, according to an example embodiment.

FIGS. 9 and 10 illustrate the rotary assembly 606 of the bottle scan and pick assembly 602, according to an example embodiment. The rotary assembly 606 may include a rotary wheel 902 and may be configured to receive and singulate bottles 302 upon entering the accumulation subsystem 404. As described in further detail below, the rotary wheel 902 may rotate among positions in which a bottle 302 is accepted from the entry conveyor 604, in which a bottle is spun by a wrap wheel while a scanner reads a bar code on the label 304 of the bottle 302, and in which a bottle 302 is picked by gripper assembly 516. The rotary wheel 902 may have a low durometer setting to allow the bottle 302 to spin within pockets of the rotary wheel 902 without damaging the label 304.

A rotary assembly motor 1001 actuates the rotary wheel 902. The rotary assembly motor 1001 may be a Rockwell Automation Kinetix VP series low inertia servo motor. Other types of motors may be used for the rotary assembly motor 1001, such as other servo motors or other motors that provide for repeatability of positioning.

The rotary wheel 902 includes pockets 906, 908, 910 configured to receive bottles 302a, 302b, 302c via the entry conveyor 604. A bottle serpentine assembly 912 may be provided, wherein the bottle serpentine assembly 912 is configured to relieve back pressure among the bottles 302a, 302b, 302c prior to entry into the pockets 906, 908, 910 of the rotary wheel 902 from the entry conveyor 604. Although the rotary wheel 902 of the embodiment of the rotary assembly 606 illustrated in FIGS. 9 and 10 includes three pockets 906, 908, 910, in other embodiments, fewer or more than three pockets may be provided in the rotary wheel 902 of the rotary assembly 606.

After the bottle 302 has been transported into a pocket 906, 908, 910 via the entry conveyor 604 and the bottle serpentine assembly 912, the rotary assembly motor 1001 may actuate the rotary wheel 902, causing it to rotate (e.g., clockwise or counterclockwise). In the embodiment illustrated in FIGS. 9 and 10, the rotary wheel 902 will turn counterclockwise. The pockets 906, 908, 910 may include bearings or free wheels to allow the bottles 302a, 302b, 302c to rotate without damaging the label 304 on the bottles 302a, 302b, 302c.

When the bottle 302b is in the pocket 906, 908, 910 at the position of the pocket 908 on FIG. 9, a wrap wheel 914, actuated by a wrap wheel motor 1002, connected to a belt 1006 and a spring loaded belt shaft 1008, may spin the bottle 302 within the pocket 908. A scanner 1004 attached to the rotary assembly 606 may be configured to read the label 304 when the bottle 302 is spun by the wrap wheel 914. The spring loaded belt shaft 1008 may accommodate different sized bottles 302 within the pocket 908.

In an example embodiment, the wrap wheel motor 1002 is brushless motor. In a particular embodiment, the wrap wheel motor 1002 is a BLH series brushless motor from Oriental Motor U.S.A. Corp. Other types of motors may be used for the wrap wheel motor 1002. In an example embodiment, the scanner 1004 is a Microscan Systems, Inc. Mini Hawk Xi imager. Other types of imagers may be used as the scanner 1004.

The reading of the label 304 enables association of the bottle 302b with a particular prescription order and holding tube (such as the holding tube 518) within the table assembly 508. After the label 304 of the bottle 302 has been read by the scanner 1004, the rotary assembly motor 1001 may actuate the rotary wheel 902, causing it to turn to the position of the pocket 910 on FIG. 9. The position of pocket 910 on FIG. 9 may be the pick position from which the bottle 302 is removed from the rotary wheel 902 by the gripper assembly 516. Sensor 916 may be attached to the rotary assembly 606 in a position above the rotary wheel 902 and configured to detect the removal of the bottle 302 from the rotary wheel 902 by the gripper assembly 516. After the bottle 302 has been removed from the rotary wheel 902, the rotary assembly motor 1001 may actuate the rotary wheel 902, causing it to turn (e.g., clockwise or counterclockwise), enabling another bottle 302 to be received within the now empty pocket 906, 908, 910 of the rotary wheel 902.

If the reading of the label 304 by the scanner 1004 fails to cause association of the bottle 302 with a particular prescription order, or if no label is detected by the scanner 1004, the bottle 302 may be selected from the pick position by the gripper assembly 516 and released into the reject bin assembly 514. For example, the bottle 302 may be released into a tube of the reject bin assembly 514 that is disposed among the holding tubes of the table assembly 508.

Figure 11:
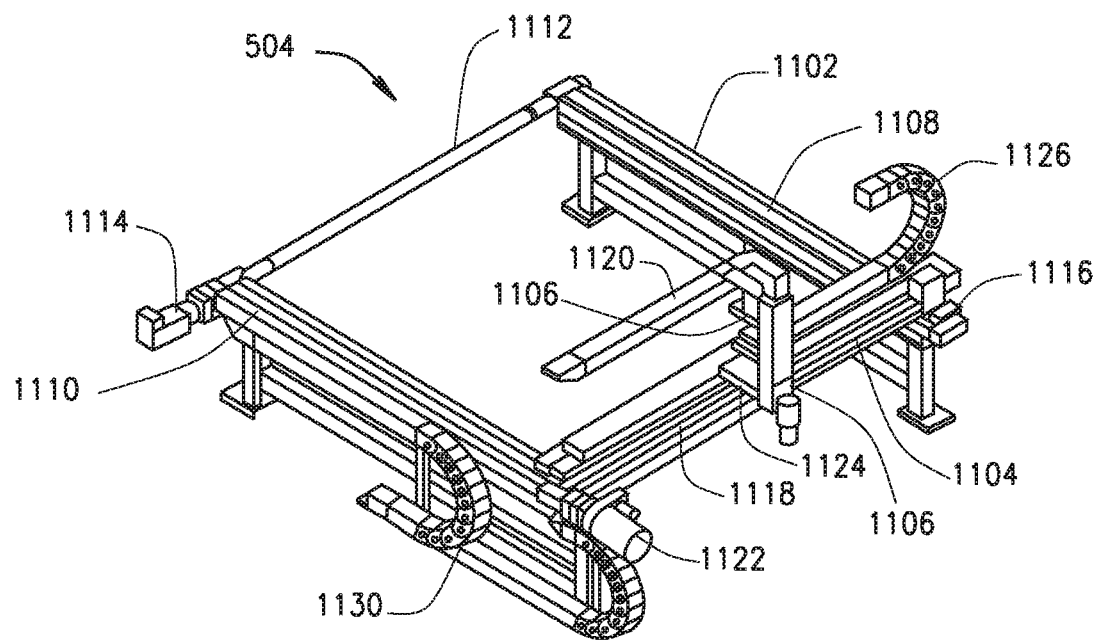
FIG. 11 is a perspective view of an upper gantry that may be deployed within the accumulation subsystem of FIG. 5, according to an example embodiment.
Figure 12:
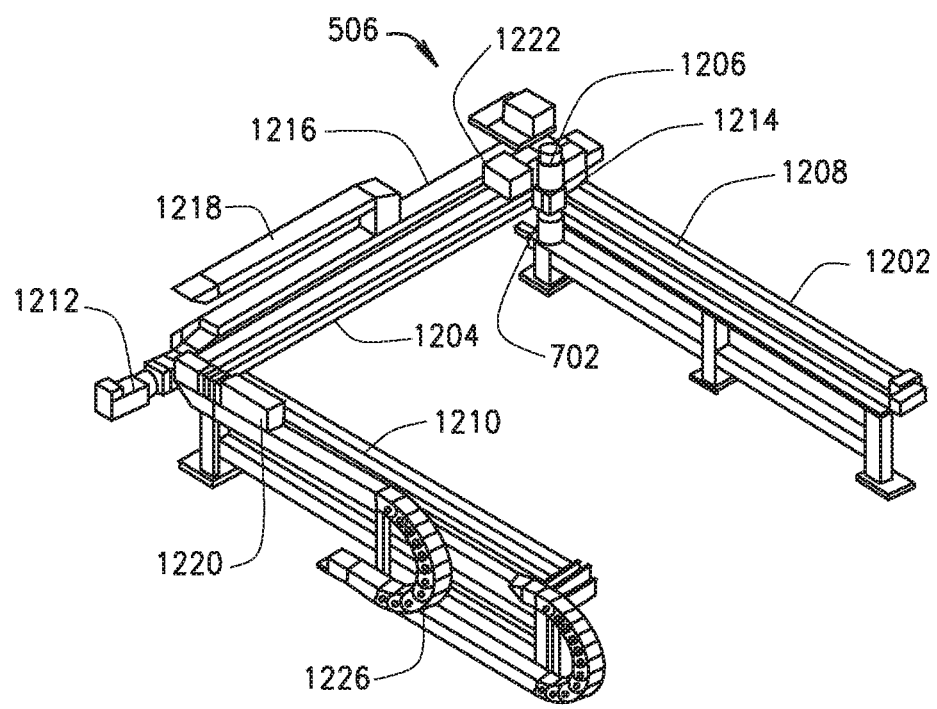
FIG. 12 is an enlarged perspective view of a lower gantry that may be deployed within the accumulation subsystem of FIG. 5, according to an example embodiment.

FIG. 11 illustrates the upper gantry 504 according to an example embodiment and FIG. 12 illustrates the lower gantry 506 according to an example embodiment. Each of the gantries 504, 506 includes an x-axis assembly 1102, 1202, a y-axis assembly 1104, 1204 and a z-axis assembly 1106, 1206. As noted above, and as described in further detail below, the gripper assembly 516 may be attached to the z-axis assembly 1106 of the upper gantry 504 and the unload assembly 702 may be attached to the z-axis assembly 1206 of the lower gantry 506.

Each x-axis assembly 1102, 1202 includes x-axis belted rails 1108, 1110, 1208, 1210. The x-axis belted rails 1108, 1110 of the upper gantry 504 are connected to one another by a connecting shaft 1112. Each x-axis assembly 1102, 1202 includes an x-axis gantry motor 1114, 1212 configured to power the x-axis belted rails 1108, 1110, 1208, 1210 and actuate the x-axis movement of the gripper assembly 516 or the unload assembly 702, as the case may be, via the upper or lower gantry, 504, 506, as the case may be. The x-axis belted rails 1108, 1110, 1208, 1210 include slides 1116, 1214 to connect the y-axis assemblies 1104, 1204 to the x-axis assemblies 1102, 1202 of the upper and lower gantries 504, 506, respectively.

Each y-axis assembly 1104, 1204 includes y-axis belted rails 1118, 1120, 1216, 1218. Each y-axis assembly 1104, 1204 includes a y-axis gantry motors 1122, 1220 configured to power the y-axis belted rails 1118, 1120, 1216, 1218 and actuate the y-axis movement of the gripper assembly 516 or the unload assembly 702, as the case may be, via the upper or lower gantry, 504, 506, as the case may be. The y-axis belted rails 1118, 1216 include slides 1124, 1222 to connect the y-axis assemblies 1104, 1204 to the z-axis assemblies 1106, 1206 of the upper and lower gantries 504, 506, respectively.

The z-axis assemblies 1106, 1206 facilitate the z-axis movement of the gripper assembly 516 and the unload assembly 702, respectively, via the upper and lower gantries, 504, 506, respectively, wherein the z-axis movement may be actuated by a motor. The z-axis assemblies 1106, 1206 in combination with the gripper assembly 516 and the unload assembly 702, respectively, are described in further detail below, in reference to FIGS. 18 and 19 and 21 and 22, respectively.

Cable guides 1126, 1128, 1130, 1224, 1226 protect cables used to control the movement of the upper and lower gantries 504, 506, e.g., via instructions provided by the control subsystem 402.

The x-axis gantry motors 1114, 1212 and the y-axis gantry motors 1122, 1220 may be servo motors. In an example embodiment, the gantry motors 1114, 1212, 1122, 1220 are Rockwell Automation Kinetix VP series low inertia servo motor. Other types of motors that have similar rates and torques, sufficient to move the equipment at a selected cycle rate and time, may be used for the gantry motors 1114, 1212, 1122, 1220.

FIGS. 13-17 illustrate a table assembly 508, or portions thereof, according to an example embodiment. The table assembly 508 may be deployed in the accumulation subsystem 404, or may otherwise be deployed.

The table assembly 508 includes multiple holding tubes, including the holding tubes 518a, 518b, 518c, 518d, which are supported by a support structure 1302. The support structure includes a base plate 1304 and an upper plate 1306.

The holding tubes 518a, 518b, 518c, 518d, may be arranged in a tube cluster 1502. The tube cluster 1502 may include a catch assembly 1402 affixed to the bottom of the holding tubes 518a, 518b, 518c, 518d in the tube cluster 1502. The catch assembly 1402 may include movable catch assembly fingers 1504a, 1504b, 1504c. Catch assembly fingers 1504a, 1504b, 1504c, when open, may obstruct the lower opening of the holding tubes 518a, 518b, 518c, 518d and, thereby, operate to retain the bottles 302 in the holding tubes 518a, 518b, 518c, 518d, respectively, of the tube cluster 1502. For example, in FIG. 15, catch assembly fingers 1508a, 1508c are illustrated in an open, obstructing position.

The catch assembly fingers 1504a, 1504b, 1504c may be hinged such that a catch assembly finger, e.g., the catch assembly finger 1504b, will move up into a finger slot 1506 upon engagement by the unload assembly 702. The finger slot 1506 is sized such that the associated catch assembly finger is completely received therein. When the catch assembly finger 1504b is released, bottles 302 held within the holding tube 518a will be released into the unload assembly tube 704 of the unload assembly 702.

Figure 13:
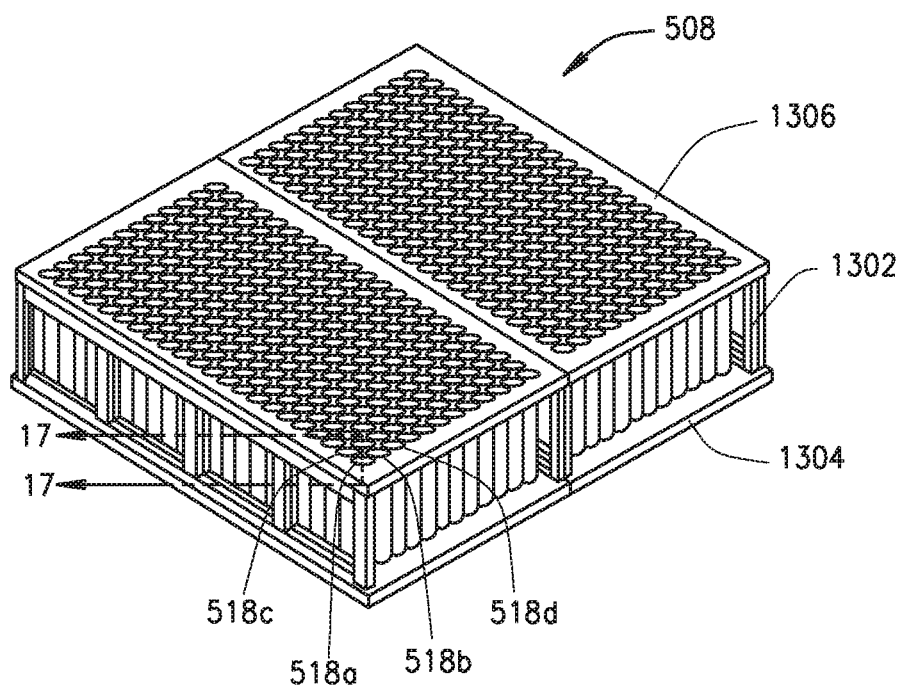
FIG. 13 is a perspective view of a table assembly that may be deployed within the accumulation subsystem of FIG. 5, according to an example embodiment.
Figure 14:
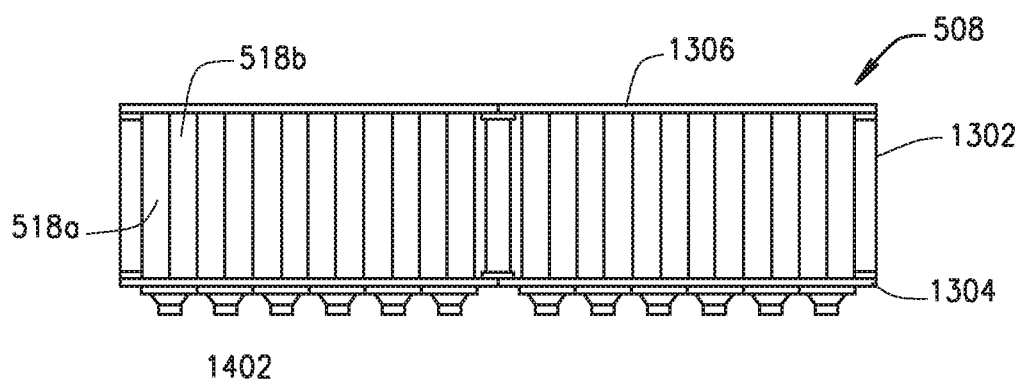
FIG. 14 is a side view of the table assembly of FIG. 13, according to an example embodiment.
Figure 15:
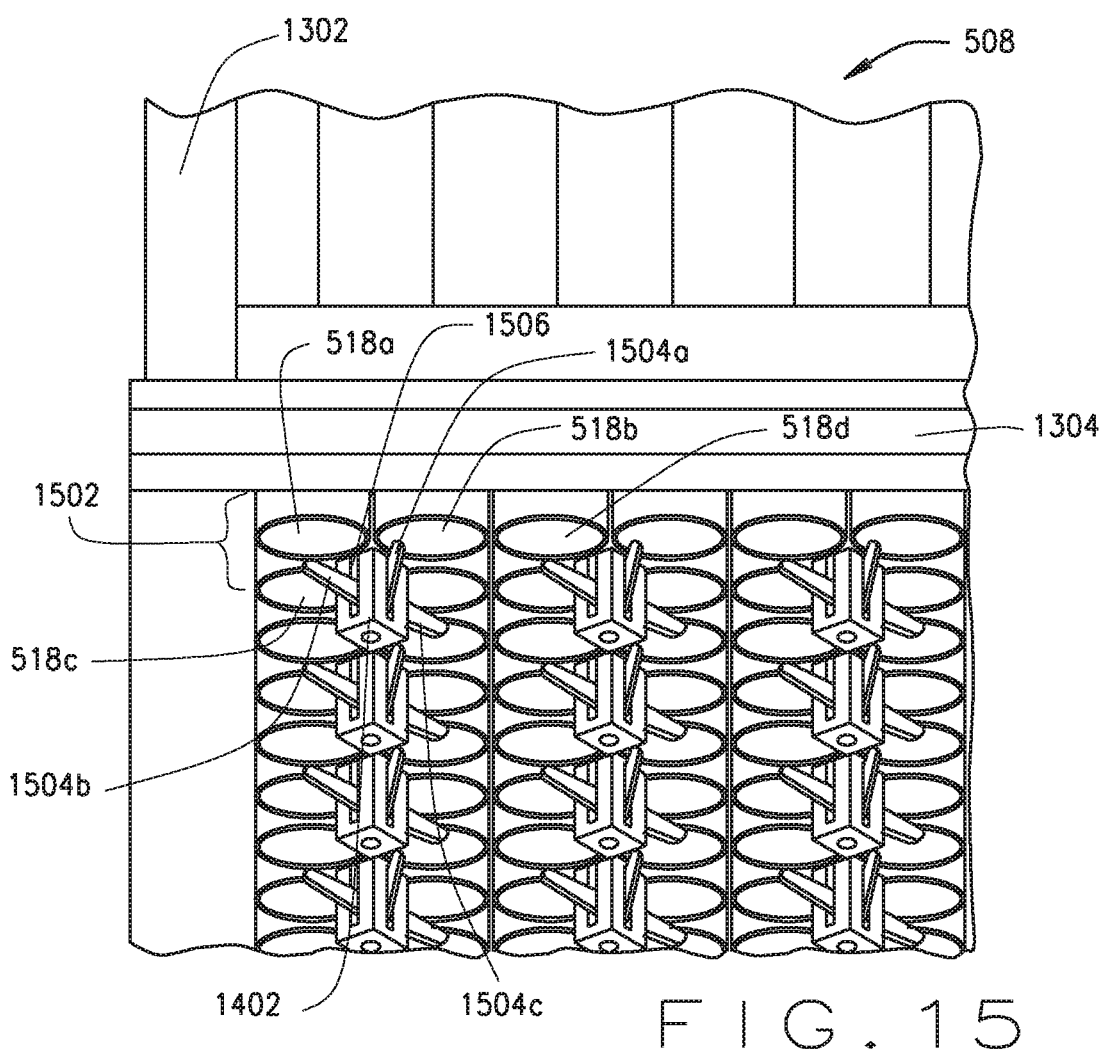
FIG. 15 is a perspective view of a portion of the table assembly of FIG. 13, according to an example embodiment.
Figure 16:
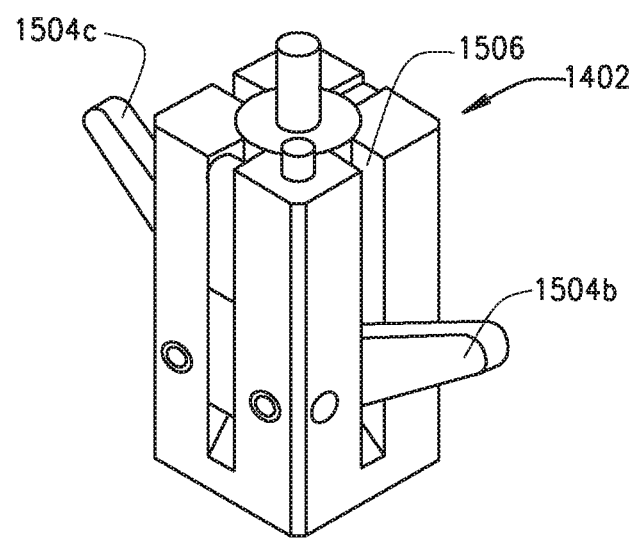
FIG. 16 is a perspective view of a catch assembly positioned within the table assembly of FIG. 13, according to an example embodiment.

The catch assembly fingers 1504a, 1504b, 1504c may be weighted such that the tip is sufficiently heavy to cause the catch assembly fingers 1504a, 1504b, 1504c to fall back to an open, obstructing position after the unload assembly 702 is removed from the holding tube 518. That is, the catch assembly fingers 1504a, 1504b, 1504c are biased into the open, obstructing position. The catch assembly fingers 1504a, 1504b, 1504c may then be urged into the closed, un-obstructing position. The catch assembly finger 1504a is illustrated in a position in which it is beginning to fall back into the open, obstructing position, after removal of the unload assembly 702. For clarity, a close-up illustration of the embodiment of the catch assembly 1402 of FIGS. 13-15 is provided as FIG. 16. In an example embodiment, the bottom of a catch assembly finger is disposed, in its open, obstructing position, at a positive angle (e.g., above the horizontal plane that would include the top of the release tube at the point at which it engages the catch assembly finger) of between approximately 22 degrees and 25 degrees. When a catch assembly finger is disposed at a positive angle in this approximate range, the catch assembly finger may lift the bottle without damaging it and fall back properly into the open, obstructing position after the unload assembly tube 704 has been removed from the holding tube 518.

Figure 17:
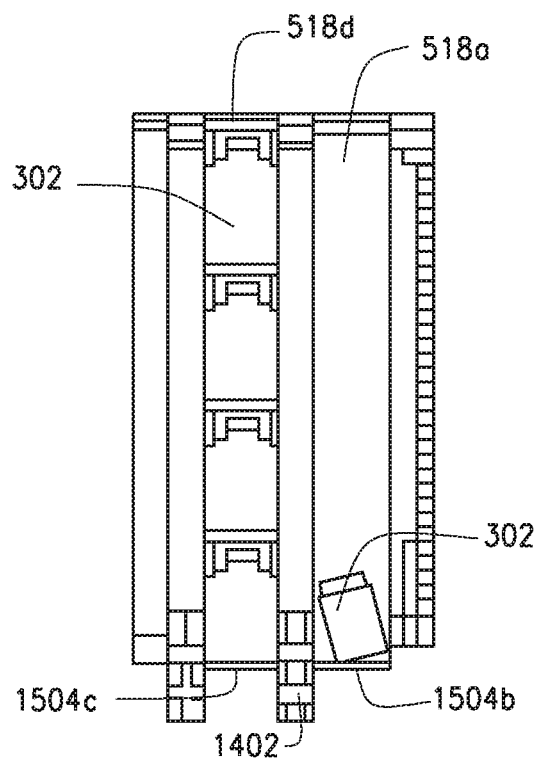
FIG. 17 is a cross-sectional view of a portion of the table assembly of FIG. 13 taken along line 17-17.

FIG. 17 illustrates a cross section of the holding tubes 518a, 518d of the table assembly 508 of FIGS. 13-15. The holding tubes 518 are each sized to hold more than one bottle 302. For example, the holding tube 518d is shown as holding four bottles 302 and the holding tube 518a is showing holding a single bottle 302. The catch assembly fingers 1504b, 1504c of the catch assembly 1402 retain the bottles 302 within the holding tubes 518a, 518d. When deployed to accumulate pharmaceutical bottles of a prescription order, all of the bottles 302 in the holding tube 518d are associated with a single prescription order. The bottle 302 in the holding tube 518a may be associated with the same prescription order as the bottles 302 in the holding tube 518d or it may be associated with a different prescription order. Each holding tube 518a, 518b, 518c, 518d is individually addressable by the accumulation device 224.

In the embodiment of FIGS. 13-15, the tube cluster 1502 includes four holding tubes 518a, 518b, 518c, 518d. In other embodiments, the quantity of holding tubes in a tube cluster may be greater than four or less than four. In an example embodiment, a tube cluster contains two holding tubes; in another example embodiment, a tube cluster contains a single holding tube; and in other example embodiments, a tube cluster contains more than four holding tubes. Each tube cluster 1502 is individually addressable by the accumulation device 224. When an individual prescription order consists of more than the number of bottles 302 that can be held in a single holding tube 518, a tube cluster 1502 may be assigned to a single prescription order.

In an example embodiment, the table assembly 508 includes at least 100 holding tubes, in another embodiment at least 250 tubes, in still another embodiment at least 400 holding tubes. In another example embodiment, the table assembly 508 includes at least 500 holding tubes. In yet another example embodiment, such as the embodiment illustrated in FIGS. 13-15, the table assembly 508 includes between 400 and 600 holding tubes. In a further embodiment, the table assembly 508 includes fewer than 400 holding tubes and, in another example embodiment, the table assembly 508 includes more than 600 holding tubes. The number of holding tubes may be based on the speed of the gantries in relation to bottle and order consolidation requirements.

In the embodiment of FIGS. 13-15, the holding tubes 518a, 518b, 518c, 518d are generally cylindrical; in other embodiments, rods can be used in place of holding tubes to hold bottles in the table assembly via points of contact around the bottles. The holding tubes 518 may be configured to receive a variety of sizes and/or shapes of bottles. In other words, the bottles may have different dimensions. The holding tubes 518 of some embodiments are configured to receive bottles 302 having different diameters. For example, the holding tubes 518 of the embodiment of the table assembly 508 illustrated in FIGS. 13-15 are configured to receive cylindrical bottles ranging in sizes from a diameter of between approximately 1.7 and 1.8 inches (with a 75 cc volume) to a diameter of between approximately 2.2 inches and 2.3 inches (with a 200 cc volume) and, when received by the holding tubes 518a, 518b, 518c, 518d, a smaller size of bottle 302 may tilt, as illustrated with respect to the holding tube 518a, but will not turn on its side, thus enabling the bottle 302 to exit the holding tube 518a and, ultimately, the accumulation subsystem 404, in an upright position. In an example, the interior diameter of the holding tube 518 is slightly larger than the largest bottle 302 that will be held within the holding tube 518. For example, the interior diameter of the holding tube 518 may be between approximately 5 percent and 6 percent larger than the exterior diameter of the largest bottle 302 that will be held within the holding tube.

In other embodiments, holding tubes may be configured to receive bottles that are smaller than approximately 1.7 inches in diameter or that are larger than approximately 2.3 inches in diameter. In the embodiment of FIGS. 13-15, the holding tubes 518a, 518b, 518c, 518d are configured to receive up to four bottles 302. In other embodiments, holding tubes may be configured to receive more than four bottles or fewer than four bottles.

Figure 18:
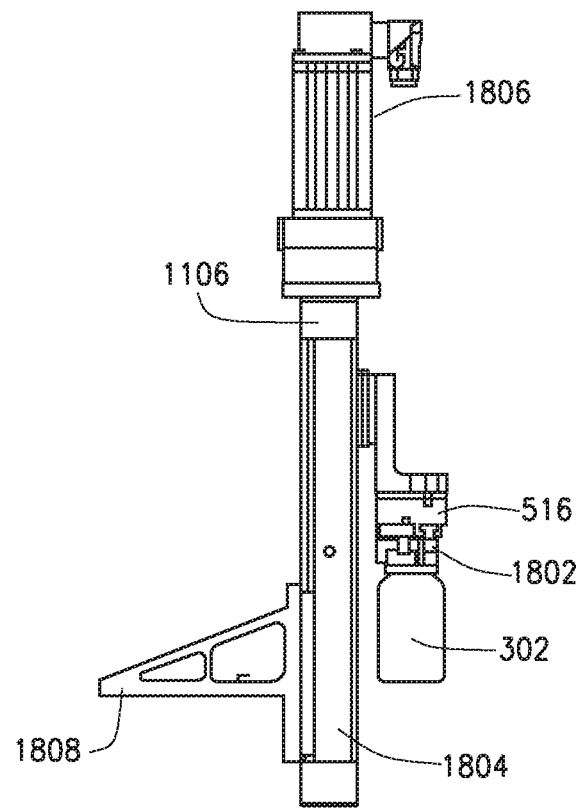
FIG. 18 is a side view of a portion of a bottle scan and pick assembly and the z-axis assembly of the upper gantry of FIG. 11.
Figure 19:
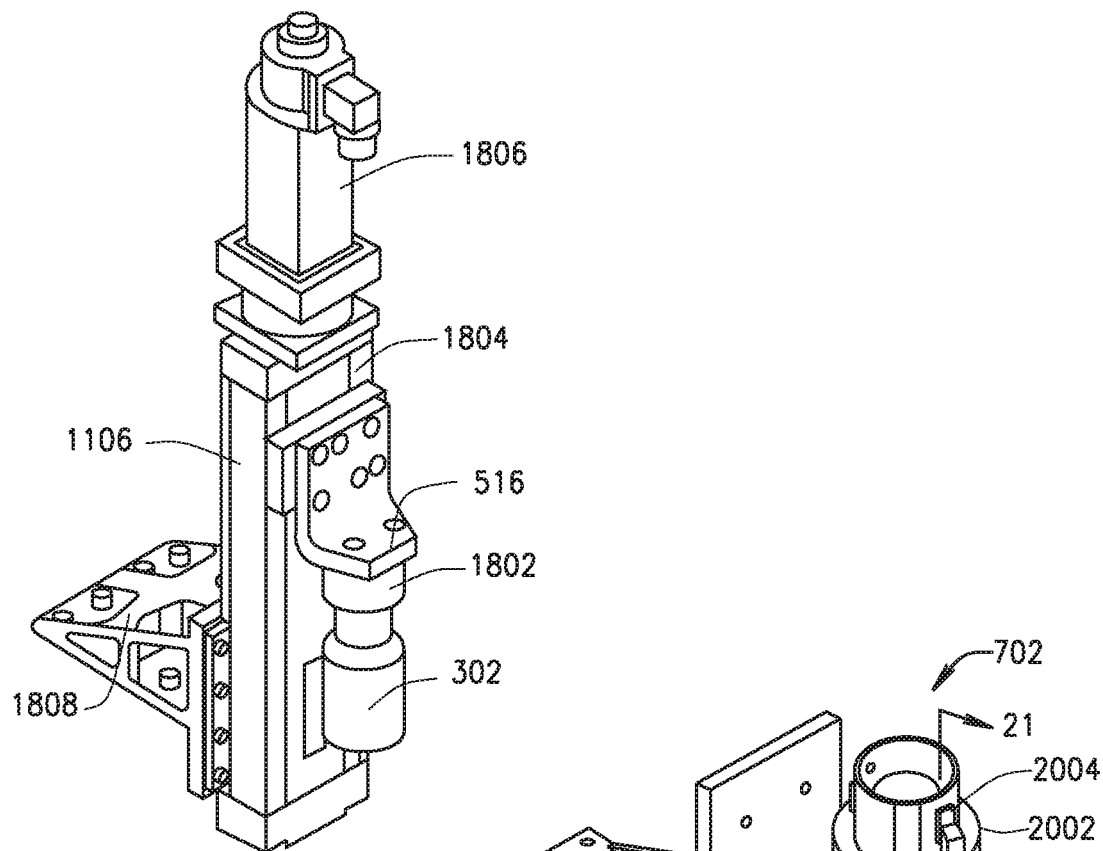
FIG. 19 is a perspective view of the portion of a bottle scan and pick assembly and the z-axis assembly of the upper gantry of FIG. 18.

FIGS. 18 and 19 illustrate the gripper assembly 516 of the bottle scan and pick assembly 602, in combination with the z-axis assembly 1106 of the upper gantry 504, according to an example embodiment. The gripper assembly 516 includes gripper jaws 1802 configured to grip a bottle 302. For example, the gripper jaws 1802 may be configured to grip a variety of sizes of caps, and at least the variety of sizes associated with the sizes of bottles 302 that will be retained in the accumulation subsystem. The gripper jaws 1802 may have a knurled surface. The gripper assembly 516 may be a pneumatic gripper in which the opening function is achieved via air input and the gripping function is achieved via springs configured to close the gripper jaws 1102 upon release of the air. In an example embodiment, the gripper assembly 516 is a pneumatic, PHD, Inc. Series GRT 3 jaw parallel gripper with a 40 mm bore, standard jaw travel, and proximity switches that is spring assist closed. Other types of grippers may be used as the gripper assembly 516, such as a spring-loaded or servo-style gripper.

The gripper assembly 516 may be mounted to a z-axis belted rail 1804 of the z-axis assembly 1106. The z-axis assembly 1106 includes a z-axis motor 1806 configured to power the z-axis belted rail 1804 and actuate the z-axis movement of the gripper assembly 516. The z-axis motor 1806 may be a Rockwell Automation Kinetix VP series low inertia servo motor. In an example embodiment, the z-axis motor 1806 is the Rockwell Automation Kinetix VP low series inertia motor model number VPL-B0752. Other motors may be used as the z-axis motor 1806.

A bracket 1808 may be used to attach the z-axis assembly 1106 and gripper assembly 516 to the slide 1124 of the y-axis assembly 1104 of the upper gantry 504.

Figure 20:
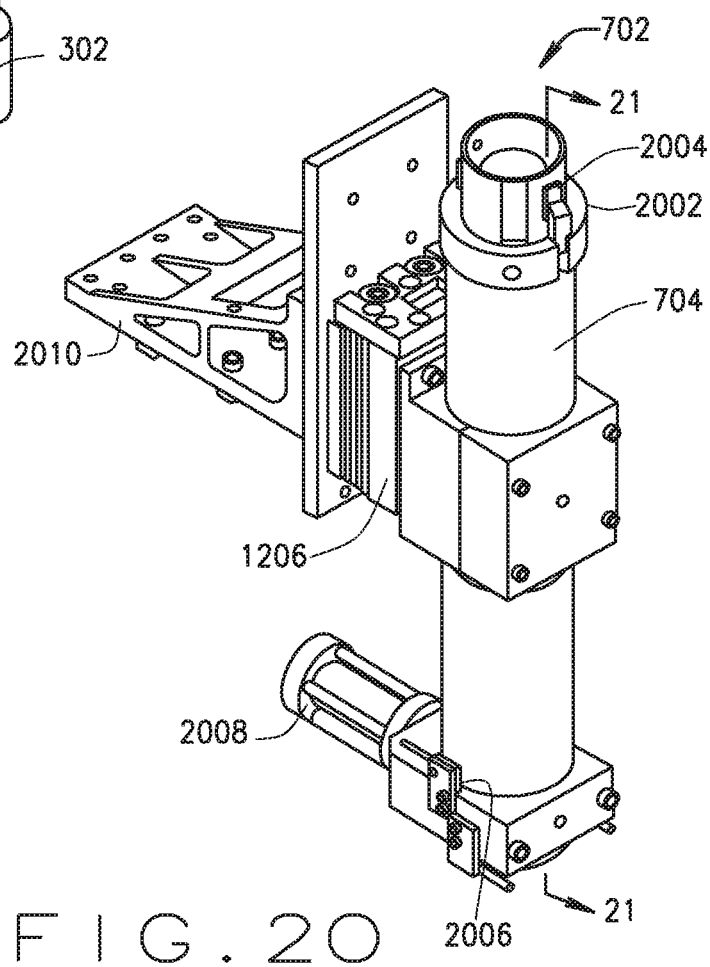
FIG. 20 is a perspective view of an unload assembly and the z-axis assembly of the lower gantry of FIG. 12.
Figure 21:
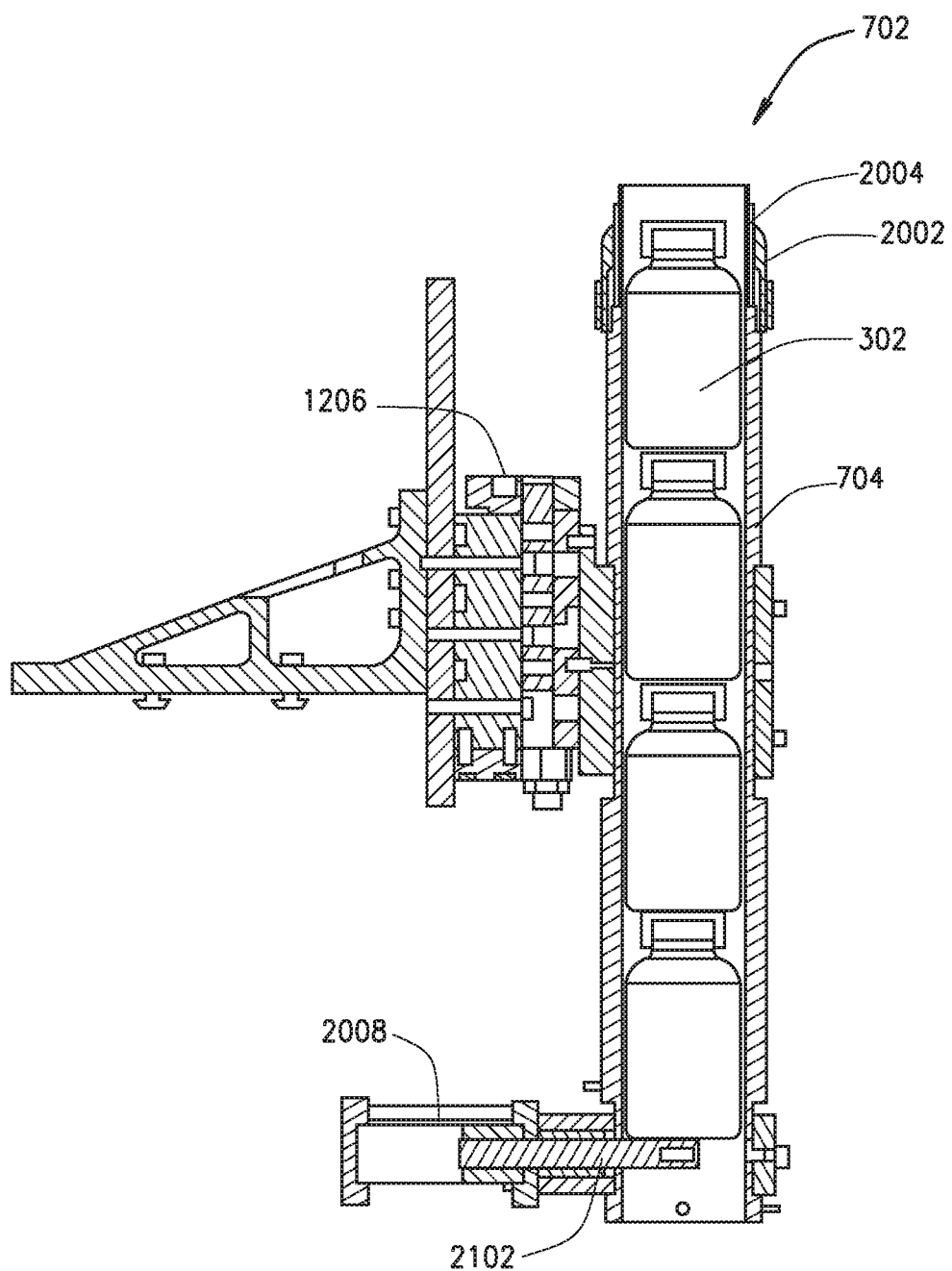
FIG. 21 is a side, cross-sectional view of the unload assembly and the z-axis assembly of the lower gantry of FIG. 20 along line 21-21 of FIG. 20.

FIGS. 20 and 21 illustrate the unload assembly 702 according to an example embodiment. The unload assembly 702 may be deployed in the accumulation subsystem 404, or may otherwise be deployed.

The unload assembly 702 includes a cup 2002 disposed at the top of the unload assembly tube 704. When the unload assembly 702 is moved up into the bottom of a holding tube, e.g., the holding tube 518d of FIG. 17, via z-axis movement of the z-axis assembly 1206 of the lower gantry 506, the cup 2002 may enter the bottom of the holding tube 518a and close the catch assembly finger 1504c into the unobstructed position, thereby releasing the bottles 302 in the holding tube 518d into the unload assembly tube 704. The cup 2002 may be removable to facilitate ease of replacement and may be formed of a durable material to minimize wear arising out of repeated engagement of the catch assembly fingers 1504a, 1504b, 1504c. In an example embodiment, the cup 2002 is formed from steel.

As shown in the embodiment of FIG. 21, an upper sensor 2004 is configured and positioned to detect bottle(s) 302 passing through the holding tube 518 into the unload assembly tube 704 after the catch assembly finger 1504a, 1504b, 1504c has been released. A lower sensor 2006 is configured and positioned to detect bottle(s) 302 passing from the unload assembly tube 704 into the lower escapement 510, 512.

If bottle(s) 302 are not detected by the upper sensor 2004, or if the bottles 302 are detected by the upper sensor 2004 but are not detected by the lower sensor 2006, an alert may be generated, e.g., by the control subsystem 402 of the accumulation device 224. An alert may be otherwise generated as a fault or jam condition.

A bottle release actuator 2008, affixed at or near the bottom of the unload assembly, actuates a bottle release rod 2102 that, when extended, as illustrated in FIG. 21, holds bottles 302 within the unload assembly tube 704 and, when retracted, releases the bottles 302 from the unload assembly tube 704 into one of the bottle escapement assemblies 510, 512. In an example embodiment, the bottle release actuator 2008 is a pneumatic cylinder. In a particular embodiment, the bottle release actuator 2008 is a Bimba Flat-I, double acting, pneumatic, single rod cylinder. Other embodiments of cylinders may be used as the bottle release actuator 2008, such as an electrically driven cylinder such as a solenoid or a cylinder with a full stroke design that includes full range of movement. The bottle release rod 2102 may have a ⅜ inch diameter. The bottle release rod 2102 may be configured to extend only when the lower sensor 2006 is clear or otherwise indicates that no bottle 302 is present in the extension path of the bottle release rod 2102.

A bracket 2010 may be used to attach the z-axis assembly 1206 and unload assembly 702 to the slide 1222 of the y-axis assembly 1204 of the lower gantry 506.

Figure 22:
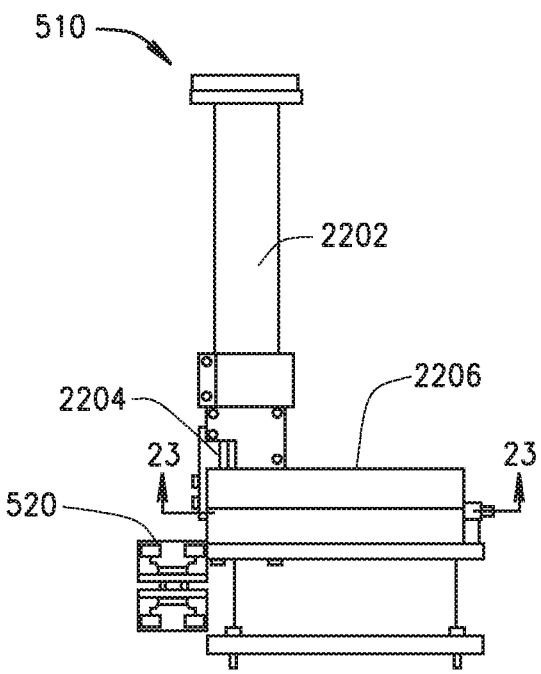
FIG. 22 is a side view of a bottle escapement assembly within the accumulation subsystem of FIG. 5, according to an example embodiment.
Figure 23:
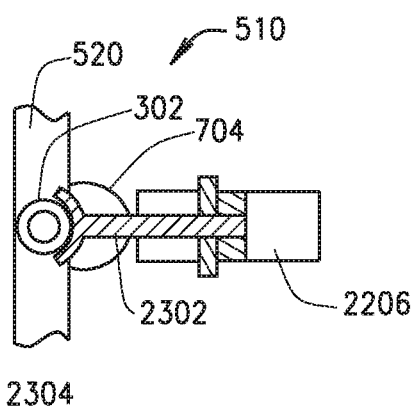
FIG. 23 is a cross-sectional view of the bottle escapement assembly along line 23-23 of FIG. 22.

FIGS. 22 and 23 illustrate the bottle escapement assembly 510 according to an example embodiment. The bottle escapement assembly 510 includes an escapement tube 2202 to receive bottle(s) 302 released from the unload assembly tube 704. An opening 2204 in the side of the escapement tube 2202 is open to the conveyor 520. An escapement rod 2302 is positioned so that when it is extended as illustrated in FIG. 23, the escapement rod 2302 forces a bottle 302 out of the escapement tube 2202, through the opening 2204 and onto the conveyor 520. The escapement rod 2302 is then retracted so that another bottle is allowed to drop to the bottom of the escapement tube 2202. The next bottle 302 is then pushed out of the opening 2204 onto the conveyor 520.

The escapement rod 2302 may include a c-shaped adaptor 2304 to facilitate retaining the bottle 302 in an upright position as it is moved out of the opening 2204 and onto the conveyor 520. The escapement rod 2302 may be actuated by a cylinder 2206. In an example embodiment, the cylinder 2206 is a pneumatic cylinder. In a particular embodiment, the cylinder is a Bimba Original Line, pneumatic, single rod cylinder. Other embodiments of cylinders may be used as the cylinder 2206.

Figure 24:
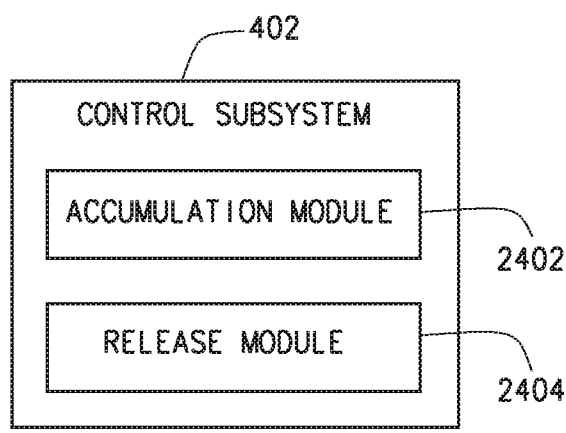
FIG. 24 is a diagram of a control subsystem within the accumulation device of FIG. 4, according to an example embodiment.

FIG. 24 illustrates an example control subsystem 402 that may be deployed in the order processing device 102, the accumulation device 224, or otherwise deployed in the system 100. One or more modules are communicatively coupled and included in the control subsystem 402 to enable control of the accumulation and/or temporary storage operations of the accumulation device 224. The modules of the control subsystem 402 that may be included are an accumulation module 2402 and a release module 2404. Other modules may also be included.

In some embodiments, the modules of the control subsystem 402 may be distributed so that some of the modules are deployed in the order processing device 102 and some modules are deployed in the accumulation device 224. In one embodiment, the modules are deployed in memory and executed by a processor coupled to the memory. The functionality contained within the modules 2402 and 2404 may be combined into a lesser number of modules, further divided among a greater number of modules, or redistributed among existing modules. Other configurations including the functionality of the modules 2402, 2404 may be used.

The accumulation module 2402 may control the operations of the scanner 1004 and, based on the data read from the label 304 of the bottle 302, may determine the holding tube 518 into which the bottle 302 will be placed. The accumulation module 2402, in some embodiments, controls the operations of the upper gantry 504 and gripper assembly 516 to perform the operations of gripping and removing the bottle 302 from the pick position of the rotary wheel 902, moving the bottle 302 to the holding tube 518 into which the particular bottle 302 is to be placed, and releasing the bottle 302 into the holding tube 518. The accumulation module 2402 may track each bottle 302 for each prescription order at each location of the bottle 302 as it travels through the system.

The accumulation module 2402 may access data, such as the order data 110, the member data 112, the claims data 114, the drug data 116, the prescription data 118, and/or the plan sponsor data 120, associated with a label 304 of a particular bottle 302. Based on such data, the accumulation module 2404 may identify the particular holding tube 518 into which the particular bottle 302 will be placed.

The release module 2404 may control the operations of the lower gantry 506 and the unload assembly 702 to perform the steps of moving the unload assembly 702 under a holding tube 518, raising the unload assembly 702 to insert the cup 2002 of the unload assembly 702 into the bottom of the holding tube 518, thereby engaging the catch assembly finger 1504a, 1504b, 1504c, causing the bottle(s) 402 to be released from the holding tube 518 into the unload assembly tube 704. The release module 2404 may control the operations of the lower gantry 506 and the unload assembly 702 to perform the steps of moving the unload assembly 702 to one of the bottle escapements 510, 512, retracting the unload rod 2102 to empty the bottle(s) from the unload assembly tube 704 into the escapement tube 2202, and extending the escapement rod 2302 to push the bottle(s) 302 through the opening 2204 and onto the conveyor 520.

The release module 2404 may access data, such as the order data 110, the member data 112, the claims data 114, the drug data 116, the prescription data 118, and/or the plan sponsor data 120, associated with a particular prescription order associated with bottle(s) 302 held in one or more holding tube 518 of the accumulation subsystem 404. Based on such data, the release module 2404 may identify a particular holding tube 518 as a holding tube from which bottle(s) should be emptied and released from the accumulation subsystem 404. Such identification may be based, for example, on a determination that all of the bottles of the particular prescription order to be accumulated at the accumulation subsystem 404 of the accumulation device 224 have been placed into one or more holding tubes 518 of the table assembly 508. In another example, such identification may be based on a determination that all of the other components of the particular prescription order that includes one or more bottles temporarily stored at the accumulation subsystem 404 have been fulfilled or are being fulfilled by another device within the system 100.

Figure 25:
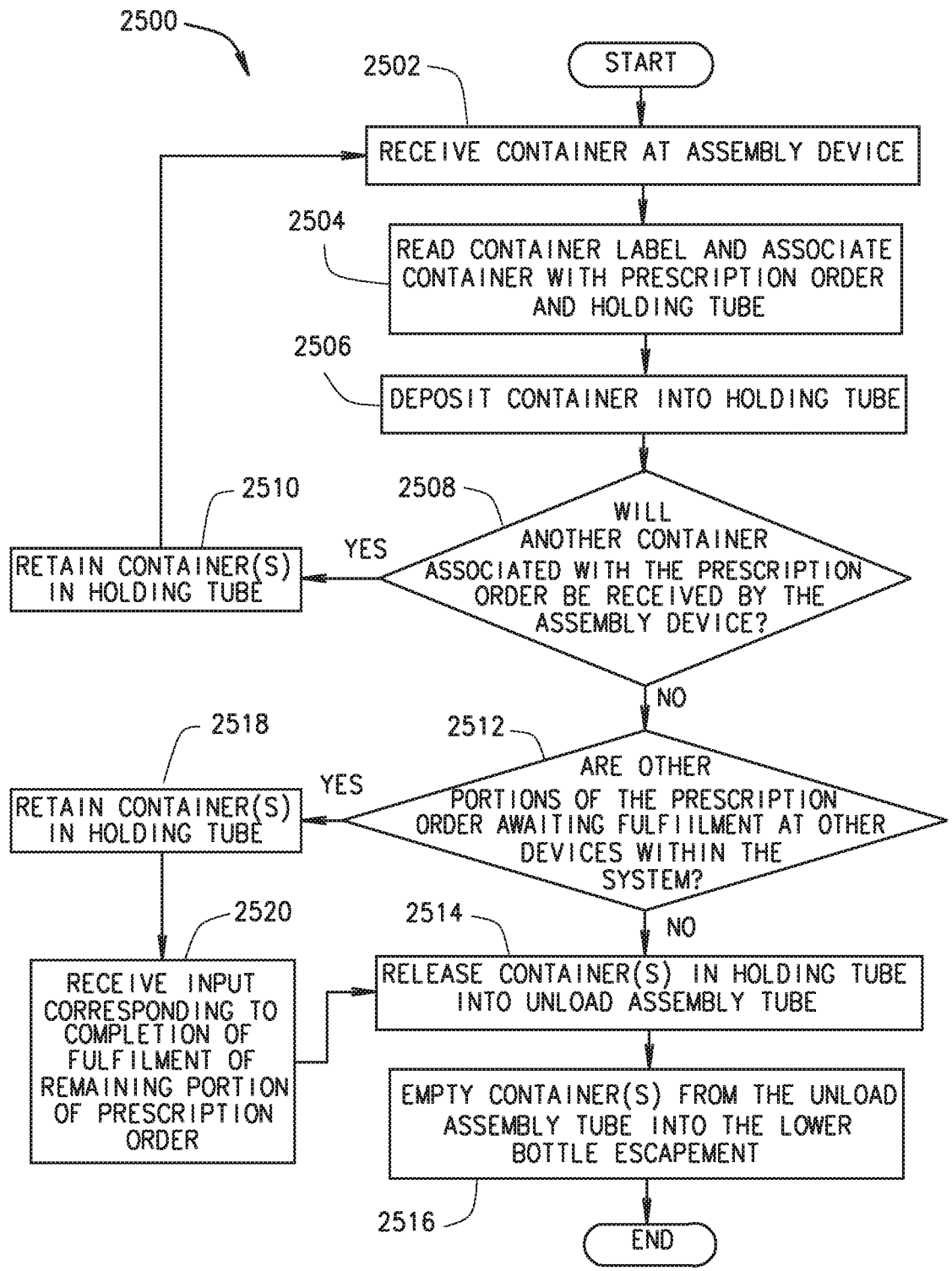
FIG. 25 is an example process flow illustrating a method of accumulating pharmaceutical bottles of a prescription order, according to an example embodiment.

FIG. 25 illustrates a method 2500 for accumulating pharmaceutical bottles of a prescription order, according to an example embodiment. The method 2500 may be performed by the accumulation device 224, partially by the order processing device 114 and partially by the accumulation device 224, or may be otherwise performed.

At block 2502, the bottle 302 is received at the accumulation device 224. The bottle label 304 is read and the bottle 302 is associated with a prescription order and a holding tube 518 at block 2504. At block 2506, the bottle 302 is deposited into the holding tube 518. If, at block 2508, another bottle 302 associated with the prescription order will be received by the accumulation device 224 then, at block 2510, the bottle will be retained in the holding tube 518. This process will continue, with additional bottles 302 of the prescription order being added to the holding tube 518, until there are no additional bottles 302 of the prescription order to be received at the accumulation device 224.

If no additional bottles 302 will be received, but, at block 2512, other portions of the prescription order are awaiting fulfilment at other devices within the system, then, at block 2514, the bottle(s) 302 will be retained in the holding tube 518 at block 2516 until, at block 2518, input corresponding to completion of fulfilment of the remaining portion of the prescription order is received by the accumulation device 224, at which point, at block 2520, the bottle(s) in the holding tube 518 will be released into the unload assembly tube 704.

If no additional bottles 302 will be received, and, at block 2512, no other portion of the prescription order is awaiting fulfillment at another device within the system 100, then, at block 2514, the bottle(s) 302 in the holding tube 518 are released into the unload assembly tube 704. Then at block 2516, the bottle(s) are emptied from the unload assembly tube 704 into the bottle escapement 510, 512.

If, at block 2512, other portions of the prescription order are awaiting fulfilment at other devices within the system, then at block 2518, the bottle(s) 302 will be retained in the holding tube 518. At block 2520, input is received corresponding to completion of fulfillment of the remaining portion of the prescription order. Then, at blocks 2514 and 2516, respectively, the bottle(s) 302 are released from the holding tube 518, into the unload assembly tube 704 and then into the bottle escapement 510, 512.

Figure 26:
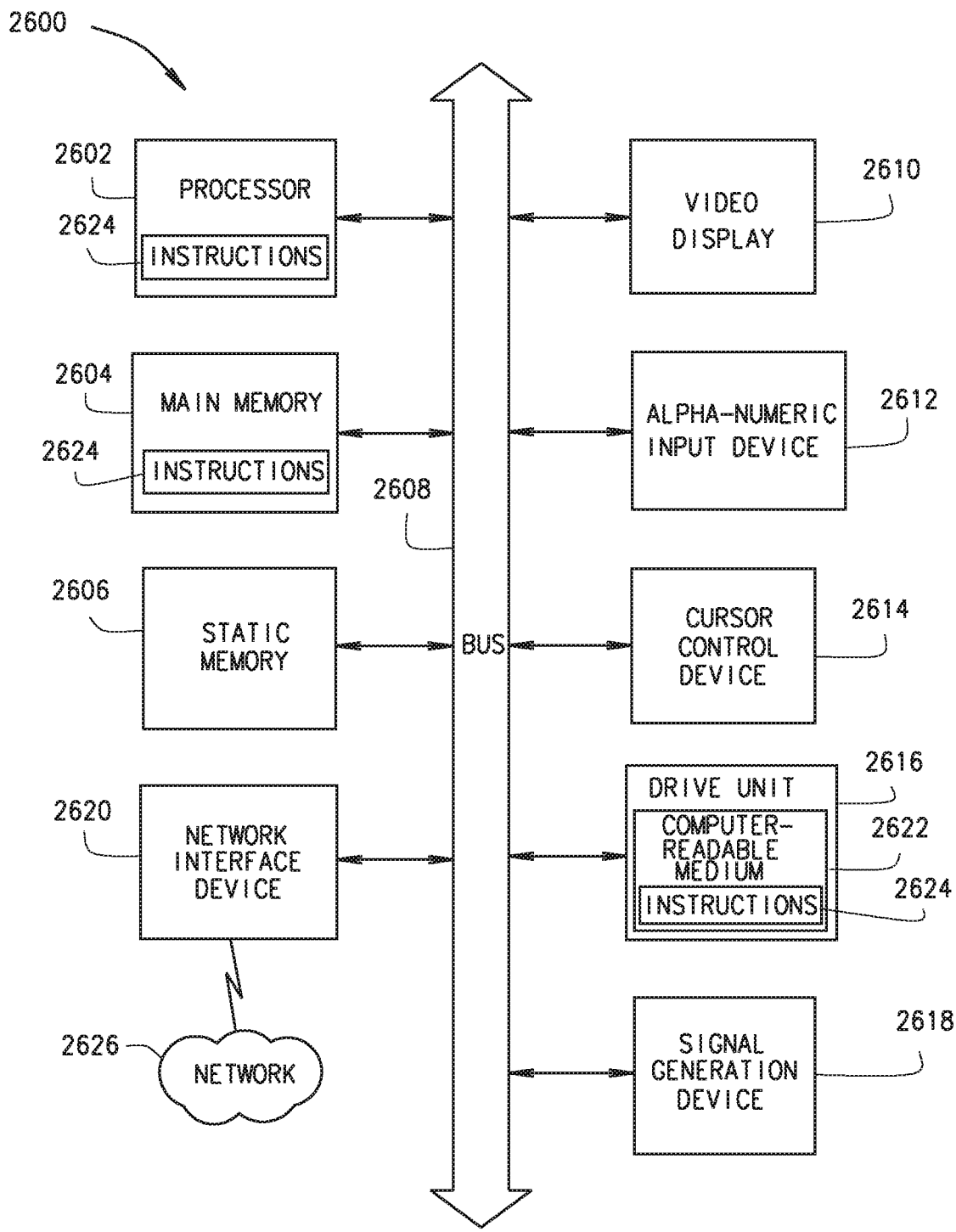
FIG. 26 is a block diagram of a machine in the example form of a computer system within which a set of instructions for causing the machine to perform any one or more of the methodologies discussed herein may be executed or stored.

FIG. 26 shows a block diagram of a machine in the example form of a computer system 900 within which a set of instructions may be executed causing the machine to perform any one or more of the methods, processes, operations, or methodologies discussed herein. The devices 102, 106-116 may include the functionality of the one or more computer systems 900. With the functionality loaded into the computer system 900 for any of the devices 102, 106-116, then the computer system 900 is a dedicated, non-general purpose machine.

In an example embodiment, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a gaming device, a set-top box (STB), a Personal Digital Assistant (PDA), a cellular telephone, a web appliance, a network router, switch or bridge, or any machine capable of executing a set of instructions sequential or otherwise) that specifies actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 2600 includes a processor 2602 (e.g., a central processing unit (CPU) a graphics processing unit (GPU) or both), a main memory 2604 and a static memory 2606, which communicate with each other via a bus 2608. The computer system 2600 further includes a video display unit 2610 (e.g., a liquid crystal display (LCD) or a cathode ray holding tube (CRT)). The computer system 2600 also includes an alphanumeric input device 2612 (e.g., a keyboard), a cursor control device 2614 (e.g., a mouse), a drive unit 2616, a signal generation device 2618 (e.g., a speaker) and a network interface device 2620.

The drive unit 2616 includes a computer-readable medium 2622 on which is stored one or more sets of instructions (e.g., software 2624) embodying any one or more of the methodologies or functions described herein. The software 2624 may also reside, completely or at least partially, within the main memory 2604 and/or within the processor 2602 during execution thereof by the computer system 2600, the main memory 2604 and the processor 2602 also constituting computer-readable media.

The software 2624 may further be transmitted or received over a network 2626 via the network interface device 2620.

While the computer-readable medium 2622 is shown in an example embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing or encoding a set of instructions for execution by the machine and that cause the machine to perform any one or more of the methodologies of the present disclosure. The term "computer-readable medium" shall accordingly be taken to include, but not be limited to, solid-state memories, and optical media, and magnetic media. In some embodiments, the computer-readable medium is a non-transitory computer-readable medium.

The term "based on" or using, as used herein, reflects an open-ended term that can reflect other elements beyond those explicitly recited.

Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled.

In an example embodiment, a pharmaceutical order filling system includes an order processing device to receive a pharmaceutical order and an accumulation device communicatively coupled to the order processing device. The accumulation device includes a bottle scan and pick assembly and a table assembly, and the bottle scan and pick assembly is configured to receive a first container of the prescription order, place the first container at a pick position, remove the first container from the pick position, and place the first container into a holding tube of the table assembly. The bottle scan and pick assembly is further configured to receive a second container of the prescription order, place the second container at a pick position, remove the second container from the pick position, and place the second container into the holding tube of the table assembly. In addition, the accumulation device includes an unload assembly with a holding tube and a bottle escapement assembly.

In another example embodiment, a pharmaceutical order filling system includes an order processing device to receive a first pharmaceutical order and a second pharmaceutical order and an accumulation device communicatively coupled to the order processing device. The accumulation device includes a bottle scan and pick assembly and a table assembly, and the table assembly includes a plurality of holding tubes arranged in a plurality of tube clusters. Each tube cluster comprises a catch assembly configured to obstruct each of the plurality of holding tubes of the tube cluster. The bottle scan and pick assembly is configured to receive a first container of the first prescription order and place the first container of the first prescription order into a first one of the plurality of holding tubes of the table assembly, and the bottle scan and pick assembly is further configured to receive a first container of the second prescription order and place the first container of the second prescription into a second one of the plurality of the holding tubes of the table assembly. The accumulation device also includes an unload assembly and a bottle escapement assembly, wherein the unload assembly is configured to empty the first container of the first prescription order from the first one of the plurality of holding tubes into an unload assembly tube and to release the first container of the first prescription order from the unload assembly tube into the bottle escapement assembly, and the unload assembly is further configured to empty the first container of the second prescription order from the second one of the plurality of holding tubes into the unload assembly tube and to release the first container of the second prescription order from the unload assembly tube into the bottle escapement assembly.

In yet another example embodiment, a method of filling a pharmaceutical order includes receiving at an order processing device a pharmaceutical orders prescribing a plurality of pharmaceuticals, filling at an automated dispensing device a first container with a quantity of a first pharmaceutical selected from the plurality of pharmaceuticals, routing the first container to an accumulation device, the accumulation device comprising a holding tube, placing the first container in the holding tube, filling at the automated dispensing device a second container with a quantity of a second pharmaceutical selected from the plurality of pharmaceuticals, routing the second container to the accumulation device, placing the second container in the holding tube to accumulate the first and second containers, releasing the accumulated first and second containers from the holding tube, and routing the first and second containers to a packing device.

The inventive subject matter may be represented in a variety of different embodiments of which there are many possible permutations.

Thus, methods and systems for accumulating prescription bottles for a prescription order are described. Although embodiments of the present invention have been described with reference to specific example embodiments, it will be evident that various modifications and changes may be made to these embodiments without departing from the broader spirit and scope of the embodiments of the invention. Accordingly, the specification and drawings are to be regarded in an illustrative rather than a restrictive sense.

The methods described herein do not have to be executed in the order described, or in any particular order. Moreover, various activities described with respect to the methods identified herein can be executed in serial or parallel fashion.

In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more than one steps within a method may be executed in different order (or concurrently) without altering the principles of the present disclosure. Further, although each of the embodiments is described above as having certain features, any one or more than one of those features described with respect to any embodiment of the disclosure can be implemented in and/or combined with features of any of the other embodiments, even if that combination is not explicitly described. In other words, the described embodiments are not mutually exclusive, and permutations of one or more than one embodiments with one another remain within the scope of this disclosure.

Spatial and functional relationships between elements (for example, between modules, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more than one intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In this application, including the definitions below, the term 'module' or the term 'controller' may be replaced with the term 'circuit.' The term 'module' may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more than one interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuitry that, in combination with additional processor circuits, executes some or all code from one or more than one modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more than one modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more than one particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory, tangible computer-readable medium.

The invention claimed is:

1. A pharmaceutical order filling system comprising:
   an order processing device to receive a prescription order; and
   an accumulation device communicatively coupled to the order processing device, the accumulation device comprising a bottle scan and pick assembly and a table assembly,
   wherein the bottle scan and pick assembly is configured to receive a first bottle of the prescription order, place the first bottle at a pick position, remove the first bottle from the pick position, and place the first bottle into a holding tube of the table assembly;
   wherein the bottle scan and pick assembly is further configured to receive a second bottle of the prescription order, place the second bottle at a pick position, remove the second bottle from the pick position, and place the second bottle into the holding tube of the table assembly; and
   the accumulation device further comprising an unload assembly and a bottle escapement assembly, wherein the unload assembly includes an unload assembly tube.

2. The pharmaceutical order filling system of claim 1, wherein the holding tube is configured to receive the first bottle and the second bottle when the diameter of the first bottle is different than the diameter of the second bottle, and wherein the bottle escapement assembly is configured to push the first and second bottles out of the bottle escapement assembly and onto a conveyor in an upright position.

3. The pharmaceutical order filling system of claim 1, wherein the bottle escapement assembly includes an escapement tube and an escapement rod, wherein the escapement tube receives the first bottle from the unload assembly tube and the escapement rod forces the first bottle out of an opening in the escapement tube onto a conveyor.

4. The pharmaceutical order filling system of claim 1, wherein the first bottle is filled at a first device of the pharmaceutical order filling system and the second bottle is filled at a second device of the pharmaceutical order filling system.

5. The pharmaceutical order filling system of claim 4, wherein the first device is an automated dispensing device and the second device is a manual fulfillment device.

6. The pharmaceutical order filling system of claim 4, wherein the first device is a first automated dispensing device and the second device is a second automated dispensing device.

7. The order processing device of claim 1, wherein the order processing device is further configured to receive a second prescription order;
   wherein the bottle scan and pick assembly is configured to receive a first bottle of the second prescription order, place the first bottle of the second prescription order at a pick position, remove the first bottle of the second prescription order from the pick position, and place the first bottle of the second prescription order into a second holding tube of the table assembly; and
   wherein the bottle scan and pick assembly is further configured to receive a second bottle of the second prescription order, place the second bottle of the second prescription order at a pick position, remove the second bottle of the second prescription order from the pick position, and place the second bottle of the second prescription order into the second holding tube of the table assembly.

8. The order processing system of claim 1, wherein the accumulation device further comprises an upper gantry and the bottle scan and pick assembly comprises a gripper assembly, and wherein the gripper assembly is mounted to a z-axis belt rail of a z-axis assembly of the upper gantry.

9. The order processing system of claim 8 wherein the z-axis assembly of the upper gantry includes a z-axis motor configured to power the z-axis belted rail and actuate z-axis movement of the gripper assembly.

10. The order processing system of claim 1, wherein the accumulation device further comprises a lower gantry, wherein the unload assembly is mounted to a z-axis assembly of the lower gantry, and wherein the z-axis assembly is configured to actuate z-axis movement of the unload assembly.

11. The order processing system of claim 10, wherein the unload assembly comprises a cup disposed at the top of the unload assembly tube and wherein the cup is configured to enter an open end of the holding tube and to engage a catch assembly finger and move the catch assembly finger from a position obstructing the open end of the holding tube into an unobstructing position when z-axis movement of the unload assembly is actuated.

12. The order processing system of claim 1, wherein the bottle scan and pick assembly further comprises a wheel assembly, wherein the wheel assembly is configured to singulate a plurality of bottles entering the accumulation device.

13. The order processing system of claim 12, wherein the wheel assembly comprises a rotary wheel and a wrap wheel, wherein a wrap wheel motor connected to a belt and a spring loaded belt shaft actuates the wrap wheel and rotates one of the bottles within a pocket of the wrap wheel.

14. The order processing system of claim 1, wherein the table assembly comprises a tube cluster and wherein the tube cluster comprises a plurality of holding tubes and a catch assembly.

15. The order processing system of claim 14, wherein the catch assembly comprises a catch assembly finger that is configured to open to a position obstructing one of the holding tubes of the tube cluster.

16. The order processing system of claim 1, wherein the table assembly further comprises a plurality of at least approximately 400 holding tubes.

17. A pharmaceutical order filling system comprising:
   an order processing device to receive a first prescription order and a second prescription order; and
   an accumulation device communicatively coupled to the order processing device, the accumulation device comprising a bottle scan and pick assembly and a table assembly, the table assembly comprising a plurality of holding tubes arranged in a plurality of tube clusters, each tube cluster of the plurality of clusters including a catch assembly configured to obstruct each of the plurality of holding tubes of the tube cluster;
   wherein the bottle scan and pick assembly is configured to receive a first bottle of the first prescription order and place the first bottle of the first prescription order into a first one of the plurality of holding tubes of the table assembly;
   wherein the bottle scan and pick assembly is further configured to receive a first bottle of the second prescription order and place the first bottle of the second prescription order into a second one of the plurality of the holding tubes of the table assembly;

the accumulation device further comprising an unload assembly and a bottle escapement assembly, wherein the unload assembly is configured to empty the first bottle of the first prescription order from the first one of the plurality of holding tubes into an unload assembly tube and to release the first bottle of the first prescription order from the unload assembly tube into the bottle escapement assembly; and wherein the unload assembly is further configured to empty the first bottle of the second prescription order from the second one of the plurality of holding tubes into the unload assembly tube and to release the first bottle of the second prescription order from the unload assembly tube into the bottle escapement assembly.

18. The pharmaceutical order filling system of claim 17, wherein the catch assembly comprises a plurality of catch assembly fingers, wherein a respective one of the catch assembly fingers is adapted to open to obstruct a respective one of the holding tubes of the tube cluster.

19. The pharmaceutical order filling system of claim 18, wherein the respective one of the catch assembly fingers is adapted to close into a finger slot to unobstruct the respective one of the holding tubes of the tube cluster.

20. The pharmaceutical order filling system of claim 19, wherein the unload assembly further comprises a cap removably attached to the top of the unload assembly tube and wherein the cap is configured to engage the respective one of the catch assembly fingers and push the respective one of the catch assembly fingers into a position that does not obstruct the respective one holding tube.

21. The pharmaceutical order filing system of claim 17 wherein the plurality of holding tubes is supported by a support structure, and wherein the support structure comprises a base plate and an upper plate.

22. The pharmaceutical order filling system of claim 17, wherein the bottle pick and scan assembly comprises a rotary assembly, wherein the rotary assembly comprises a rotary wheel, wherein the rotary wheel comprises a pocket to receive the first bottle, and wherein a rotary assembly motor actuates the rotary wheel.

23. A method of filling a pharmaceutical order comprising:

receiving at an order processing device a pharmaceutical order prescribing a plurality of pharmaceuticals;

filling at an automated dispensing device a first bottle with a quantity of a first pharmaceutical selected from the plurality of pharmaceuticals;

routing the first bottle to an accumulation device, the accumulation device comprising a holding tube;

placing the first bottle in the holding tube;

filling at the automated dispensing device a second bottle with a quantity of a second pharmaceutical selected from the plurality of pharmaceuticals;

routing the second bottle to the accumulation device;

placing the second bottle in the holding tube to accumulate the first and second bottles;

releasing the accumulated first and second bottles from the holding tube; and routing the first and second bottles to a packing device.

24. The method of claim 23 further comprising capping each the first bottle and the second bottles at a capping device before it is routed to the accumulation device.

25. The method of claim 23 further comprising selecting a prepackaged quantity of a third pharmaceutical selected from the plurality of pharmaceuticals from a unit of use device;

wherein the step of releasing the accumulated first and second bottles from the holding tube is associated with the step of selecting the prepackaged quantity of the third pharmaceutical selected from the plurality of pharmaceuticals from the unit of use device, and routing the selected prepackaged quantity of the third pharmaceutical to the packing device.

26. The method of claim 25, wherein the step of releasing the accumulated first and second bottles from the holding tube comprises engaging a catch assembly finger that is obstructing the holding tube with an unload assembly tube.

27. The method of claim 23, the second container having a diameter different than the first container.

* * * * *